(12) United States Patent
Kim et al.

(10) Patent No.: US 8,261,598 B2
(45) Date of Patent: Sep. 11, 2012

(54) APPARATUS FOR PERFORMING A REACTION IN A DROPLET AND METHOD OF USING THE SAME

(75) Inventors: Nam Yong Kim, Singapore (SG); Jackie Yi Ru Ying, Singapore (SG); Yong Yeow Lee, Singapore (SG); Kwong Joo Leck, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 636 days.

(21) Appl. No.: 12/282,162

(22) PCT Filed: Mar. 9, 2006

(86) PCT No.: PCT/SG2006/000050
§ 371 (c)(1),
(2), (4) Date: Jan. 22, 2009

(87) PCT Pub. No.: WO2007/102785
PCT Pub. Date: Sep. 13, 2007

(65) Prior Publication Data
US 2010/0000304 A1 Jan. 7, 2010

(51) Int. Cl.
*G01N 1/00* (2006.01)
(52) U.S. Cl. ............... 73/64.56; 73/864.81; 422/502
(58) Field of Classification Search ............ 73/64.56, 73/64.48, 64.52; 422/400–429, 500–570; 435/284.1–309.4; 436/180
See application file for complete search history.

(56) References Cited

U.S. PATENT DOCUMENTS
3,754,872 A 8/1973 Zauft
(Continued)

FOREIGN PATENT DOCUMENTS
EP 0 812 693 A1 12/1997
(Continued)

OTHER PUBLICATIONS

Asberg, et al., "Surface Energy Modified Chips for Detection of Conformational States and Enzymatic Activity in Biomolecules," Langmuir (2006), vol. 22, No. 5, pp. 2205-2211.
(Continued)

*Primary Examiner* — Hezron E Williams
*Assistant Examiner* — Hoang Nguyen
(74) *Attorney, Agent, or Firm* — Morgan, Lewis & Bockius LLP

(57) ABSTRACT

An apparatus for processing a biological and/or chemical sample in a liquid droplet (1) is provided. The apparatus includes a processing compartment (20), a base (21) and at least one circumferential wall (25). The processing compartment (20) is defined by at least a part of the base (21), at least a part of the circumferential wall (25) and an inlet member (4). The inlet member (4) is located on top of the processing compartment (20), and includes at least one droplet inlet channel (3), which extends through the inlet member (4) and includes a contraction (2) between the inlet opening (28) of the droplet inlet channel (3) to the environment and the outlet opening (27) to the processing compartment (20). There is furthermore provided a method of processing a biological and/or chemical sample in a liquid droplet (1). The method includes disposing a medium into the processing compartment (20) of the apparatus of the invention that is immiscible with the liquid droplet (1), so that the contraction (2) is immersed in the medium. The droplet (1) is disposed into the droplet inlet channel (3) such that it is located below the contraction (2) of the droplet inlet channel (3). A process is performed on the biological and/or chemical sample in the droplet (1).

20 Claims, 10 Drawing Sheets

U.S. PATENT DOCUMENTS

| | | | | |
|---|---|---|---|---|
| 5,219,528 | A | * | 6/1993 | Clark .......................... 422/527 |
| 5,506,121 | A | | 4/1996 | Skerra et al. ................. 435/69.7 |
| 5,560,811 | A | * | 10/1996 | Briggs et al. ................. 204/451 |
| 6,086,825 | A | * | 7/2000 | Sundberg et al. ............ 422/507 |
| 6,103,493 | A | | 8/2000 | Skerra et al. ................. 435/69.1 |
| 6,130,098 | A | | 10/2000 | Handique et al. |
| 6,238,626 | B1 | * | 5/2001 | Higuchi et al. ............... 422/526 |
| 6,331,441 | B1 | * | 12/2001 | Balch et al. .................. 436/518 |
| 6,565,813 | B1 | | 5/2003 | Garyantes |
| 6,578,952 | B1 | * | 6/2003 | Sugiyama et al. ............. 347/65 |
| 6,664,044 | B1 | | 12/2003 | Sato ................................ 435/6 |
| 6,716,629 | B2 | | 4/2004 | Hess et al. ................. 435/287.2 |
| 7,163,823 | B2 | | 1/2007 | Patno et al. ............... 435/287.2 |
| 7,344,877 | B1 | | 3/2008 | Camacho et al. |
| 2003/0083474 | A1 | | 5/2003 | Schmidt .................. 530/388.25 |
| 2003/0113813 | A1 | | 6/2003 | Heidaran et al. .............. 435/7.2 |
| 2003/0209560 | A1 | | 11/2003 | Hui et al. .......................... 222/1 |
| 2004/0106191 | A1 | | 6/2004 | Muser ....................... 435/304.3 |
| 2004/0136876 | A1 | | 7/2004 | Fouillet et al. ................ 422/100 |
| 2004/0208792 | A1 | | 10/2004 | Linton et al. ................... 422/99 |
| 2004/0234966 | A1 | | 11/2004 | Bryning et al. .................. 435/6 |
| 2005/0045539 | A1 | | 3/2005 | Yu et al. ........................ 210/143 |
| 2006/0013031 | A1 | | 1/2006 | Ravkin et al. |
| 2006/0051249 | A1 | | 3/2006 | Knebel et al. |
| 2006/0105453 | A1 | | 5/2006 | Brenan et al. ................. 435/325 |
| 2007/0003448 | A1 | | 1/2007 | Kanigan et al. ............... 422/102 |
| 2008/0003671 | A1 | | 1/2008 | Martin ....................... 435/304.1 |
| 2010/0000304 | A1 | | 1/2010 | Kim et al. .................... 73/64.56 |

FOREIGN PATENT DOCUMENTS

| | | |
|---|---|---|
| EP | 1 358 939 A2 | 11/2003 |
| EP | 1473079 | 11/2004 |
| EP | 1386657 | 1/2006 |
| EP | 1683571 | 7/2006 |
| EP | 1788047 | 5/2007 |
| GB | 1 291 610 A | 10/1972 |
| JP | 3120453 | 12/1998 |
| JP | 2002/502955 | 1/2002 |
| JP | 2003-033177 A | 2/2003 |
| JP | 2004-020280 A | 1/2004 |
| JP | 2004-077476 A | 3/2004 |
| JP | 2004-535176 | 11/2004 |
| JP | 2005-3803 | 1/2005 |
| JP | 2005-099004 A | 4/2005 |
| WO | WO 96/23879 | 8/1996 |
| WO | WO 98/47003 | 10/1998 |
| WO | WO 98/55852 A1 | 12/1998 |
| WO | WO 99/39829 | 8/1999 |
| WO | WO 99/55826 | 11/1999 |
| WO | WO 00/14311 A1 | 3/2000 |
| WO | WO 00/58735 A2 | 10/2000 |
| WO | WO 01/04144 | 1/2001 |
| WO | WO 03/029462 | 4/2003 |
| WO | WO 2004/030820 | 4/2004 |
| WO | WO 2004/111610 | 12/2004 |
| WO | WO 2005/019254 | 3/2005 |
| WO | WO 2005/019255 | 3/2005 |
| WO | WO 2005/019256 | 3/2005 |
| WO | WO 2006/004739 A2 | 1/2006 |
| WO | WO 2006/046699 | 5/2006 |
| WO | WO 2008/063136 | 5/2008 |
| WO | WO 2010/120249 A1 | 10/2010 |
| WO | WO 2012/011877 A2 | 1/2012 |

OTHER PUBLICATIONS

Beck, et al., "Improving stamps for 10 nm level wafer scale nanoimprint lithography," Microelectron. Eng. (2002), vols. 61-62, pp. 441-448.

Benor, et al., "Microstructuring by microcontact printing and selective surface dewetting," J. Vac. Sci. Technol. B (2007), vol. 25, No. 4, pp. 1321-1326.

Beste, et al., "Small antibody-like proteins with prescribed ligand specificities derived from the lipocalin fold," Proc. Natl. Acad. Sci. USA (1999), vol. 96, pp. 1898-1903.

Biffinger, et al., "The Polar Hydrophobicity of Fluorinated Compounds," ChemBioChem (2004), vol. 5, pp. 622-627.

Burbulis, et al., "Quantifying small numbers of antibodies with a near-universal protein-DNA chimera," Nature Methods (2007, DOI: 10.1038/NMETH1127), 3 pages.

Chiriac, et al., "Magnetic GMI sensor for detection of biomolecules," J. Magn. Magn. Mater. (2005), vol. 293, pp. 671-676.

Churaev, et al., "Wetting of low-energy surfaces," Adv. Colloid Interfac. Sci. (2007),vol. 134-135, pp. 15-23.

Daniel, et al., "Vibration-Actuated Drop Motion on Surfaces for Batch Microfluidic Processes," Langmuir, (2005),vol. 21, pp. 4240-4248.

Dill, et al., "Modeling Water, the Hydrophobic effect, and Ion Solvation," Annu. Rev. Biophys. Biomol. Struct. (2005), vol. 34, pp. 173-199.

Gao, et al., "A Commercially Available Perfectly Hydrophobic Material," Langmuir (2007), vol. 23, No. 18, pp. 9125-9127.

Gascoyne, et al., "Dielectrophoresis-based programmable fluidic processors," Lab-on-a-Chip (2004), vol. 4, pp. 299-309.

Genua, et al., "Functional patterns obtained by nanoimprinting lithography and subsequent growth of polymer brushes," Nanotechnology (2007), vol. 18, 215301, 7 pages.

Gill, et al., "Biopharmaceutical drug discovery using novel protein scaffolds," Curr. Opin. Biotech. (2006), vol. 17, pp. 653-658.

Giovambattista, et al., "Effect of Surface Polarity on Water Contact Angle and Interfacial Hydration Structure," J. Phys. Chem. B (2007), vol. 111, pp. 9581-9587.

Goddard, et al., "Polymer surface modification for the attachment of bioactive compounds," Prog. Polym. Sci. (2007), vol. 32, No. 7, pp. 698-725.

Griffiths, et al., "Miniaturising the laboratory in emulsion droplets," Trends in Biotechnol. (2006), vol. 24, No. 9, pp. 395-402.

Herrmann, et al., "Enzymatically-generated fluorescent detection in micro-channels with internal magnetic mixing for the development of parallel microfluidic ELISA," Lab Chip (2006), vol. 6, pp. 555-560.

Holt, et al., "Domain antibodies: proteins for therapy," Trends Biotechnol. (2003), vol. 21, No. 11, pp. 484-490.

Hütten, et al., "New magnetic nanoparticles for biotechnology," J. Biotech. (2004), vol. 112, pp. 47-63.

Iliades, et al., "Triabodies: single chain Fv fragments without a linker form trivalent trimers," FEBS Lett. (1997), vol. 409, pp. 437-441.

Jakobs, et al., "Micrometer scale gel patterns," Colloids & Surfaces A: Physciochem. Eng. Aspects (2006), vol. 290, pp. 33-40.

Jung, et al., "Wetting transition of water droplets on superhydrophobic patterned surfaces," Scripta Mater. (2007), vol. 57, pp. 1057-1060.

Kanta, et al., "Preparation of Silica-on-Titania Patterns with a Wettability Contrast," Langmuir (2005), vol. 21, pp. 5790-5794.

Kwon, et al., "Quantitative Evaluation of the Relative Cell Permeability of Peptoids and Peptides," J. Am. Chem. Soc. (2007) vol. 129, pp. 1508-1509.

Kusumaatmaja, et al., "Controlling Drop Size and Polydispersity Using Chemically Patterned Surfaces," Langmuir (2007) vol. 23, pp. 956-959.

Li, et al., "What do we need for a superhydrophobic surface? A review on the recent progress in the preparation of superhydrophobic surfaces," Chem. Soc. Rev. (2007) vol. 36, pp. 1350-1368.

Lundgren, et al., "Modeling of Wetting: A Study of Nanowetting at Rough and Heterogeneous Surfaces," Langmuir (2007), vol. 23, pp. 1187-1194.

Ma, et al., "Superhydrophobic surfaces," Curr. Opin. Colloid in 11 (2006), pp. 193-202.

Mardare, et al., "Microelectrochemical lithography: A method for direct writing of surface oxides," Electrochimica Acta (2007), vol. 52, pp. 7865-7869.

Matsuda, et al., "Phosphorylcholine-endcapped oligomer and block co-oligomer and surface biological reactivity," Biomaterials (2003), vol. 24, pp. 4517-4527.

Meyer, et al., "Recent progress in understanding hydrophobic interactions," Proc. Natl. Acad. Sci. U.S.A (2006), vol. 103, No. 43, pp. 15739-15746.

Mosavi, et al., "The ankyrin repeat as molecular architecture for protein recognition," Protein Science (2004), vol. 13, No. 6, pp. 1435-1448.

Opdahl, et al., "*Polymer Surface Science*," The Chemical Record (2001), vol. 1, pp. 101-122.

Pollack, et al., "*Electrowetting-based actuation of liquid droplets for microfluidic applications*," Appl. Phys. Lett. (2000), vol. 77, pp. 1725-1726.

Popp, et al., "*Sortagging: a versatile method for protein labeling*," Nat. Chem. Bio. (2007) vol. 3, No. 11, pp. 707-708.

Rastogi, et al., "*Development and evaluation of realistic microbioassays in freely suspended droplets on a chip*," Biomicrofluidics (2007), vol. 1, pp. 014107-1-014107-17.

Ronaghi, et al., "*Pyrosequencing Sheds Light on DNA Sequencing*," Genome Research (2001), vol. 11, pp. 3-11.

Roach, et al., "*Controlling Nonspecific Protein Adsorption in a Plug-Based Microfluidic System by Controlling Interfacial Chemistry Using Fluorous-Phase Surfactants*," Anal. Chem. (2005), vol. 77, pp. 785-796.

Rose, D., "Microdispensing technologies in drug discovery," Drug Discovery Today (1999), vol. 4, No. 9, pp. 411-419.

Satriano, et al., "*Bacterial adhesion onto nanopatterned polymer surfaces*," Mat. Sci. & Eng. C (2006), vol. 26, pp. 942-946.

Silverman, et al., "*Multivalent avimer proteins evolved by exon shuffling of a family of human receptor domains*," Nat. Biotechno. (2005), vol. 23, No. 12, pp. 1556-1561.

Skerra, et al., "*Engineered protein scaffolds for molecular recognition*," J. Mol. Recognit. (2000) vol. 13, pp. 167-187.

Song, et al., "*Miniature biochip system for detection of Escherichia coli 0157:H7 based on antibody-immobilized capillary reactors and enzyme-linked immunosorbent assay*," Anal. Chim. Acta (2004), vol. 507, pp. 115-121.

Stephenson, et al., "*Quantifinng the Hydrophobic Effect. 1. A Computer Simulation-Molecular-Thermodynamic Model for the Self-Assembly of Hydrophobic and Amphiphilic Solutes in Aqueous Solution*," J. Phys. Chem. B. (2007) vol. 111, pp. 1025-1044.

Stone, et al., "*The assembly of single domain antibodies into bispecific decavalent molecules*," J. Immunol. Methods (2007), vol. 318, pp. 88-94.

Sundberg, et al., "*Contact angle measurements by confocal microscopy for non-destructive microscale surface characterization*," J. Colloid Interfac. Sci. (2007), vol. 313, pp. 454-460.

Van Oss, et al., "*Long-range and short-range mechanisms of hydrophobic attraction and hydrophilic repulsion in specific and aspecific interactions*," J Mol. Recognit. (2003), vol. 16, pp. 177-190.

Wang, et al., "*Flow-Focusing Generation of Monodisperse Water Droplets Wrapped by Ionic Liquid on Microfluidic Chips: From Plug to Sphere*," Langmuir (2007), vol. 23, pp. 11924-11931.

Wang, et al., "*In Situ Wilhelmy Balance Surface Energy Determination of Poly(3-hexylthiophene) and Poly(3,4-ethylenedioxythiophene) during Electrochemical Doping-Dedoping*," Langmuir (2006), vol. 22, pp. 9287-9294.

West, et al., "*Microplasma writing for surface-directed millifluidics*," Lab Chip (2007), vol. 7, pp. 981-983.

Widom, et al., "*The hydrophobic effect*," Phys. Chem. Chem. Phys. (2003), vol. 5, pp. 3085-3093.

Wixforth, et al., "*Flatland fluidics*," MST News (2002), No. 5, pp. 42-43.

Roach, et al., "*Controlling Nonspecific Protein Adsorption in a Plug-Based Microfluidic System by Controlling Interfacial Chemistry Using Fluorous-Phase Surfactants*," Analytical Chemistry, vol. 77, No. 3, pp. 785-796, Feb. 1, 2005.

Washizu,. M., "*Electrostatic Actuation of Liquid Droplets for Microreactor Applications*," IEEE Transactions on Industry Applications, vol. 34, No. 4, Jul./Aug. 1998.

Australian Patent Office; Authorized Officer: Jayati Ray, *Written Opinion of the International Searching Authority*, International Application No. PCT/SG2007/000393, dated Feb. 20, 2008, 3 pages.

International Search Report and Written Opinion for International Application PCT/SG2006/000050 dated May 8, 2006.

International Search Report and Written Opinion for International Application PCT/SG2011/000263 dated Feb. 29, 2012.

International Search Report and Written Opinion for International Application PCT/SG2010/000153 dated Sep. 17, 2010.

Supplementary European Search Report for EP 07 83 5548 dated Jun. 30, 2010.

Luca, D., "Preparation of TiOx Thin Films by Reactive Pulsed-Laser Ablation", Apr. 2005, Journal of Optoelectronics and Advanced Materials, vol. 7, No. 2, pp. 625-630.

\* cited by examiner

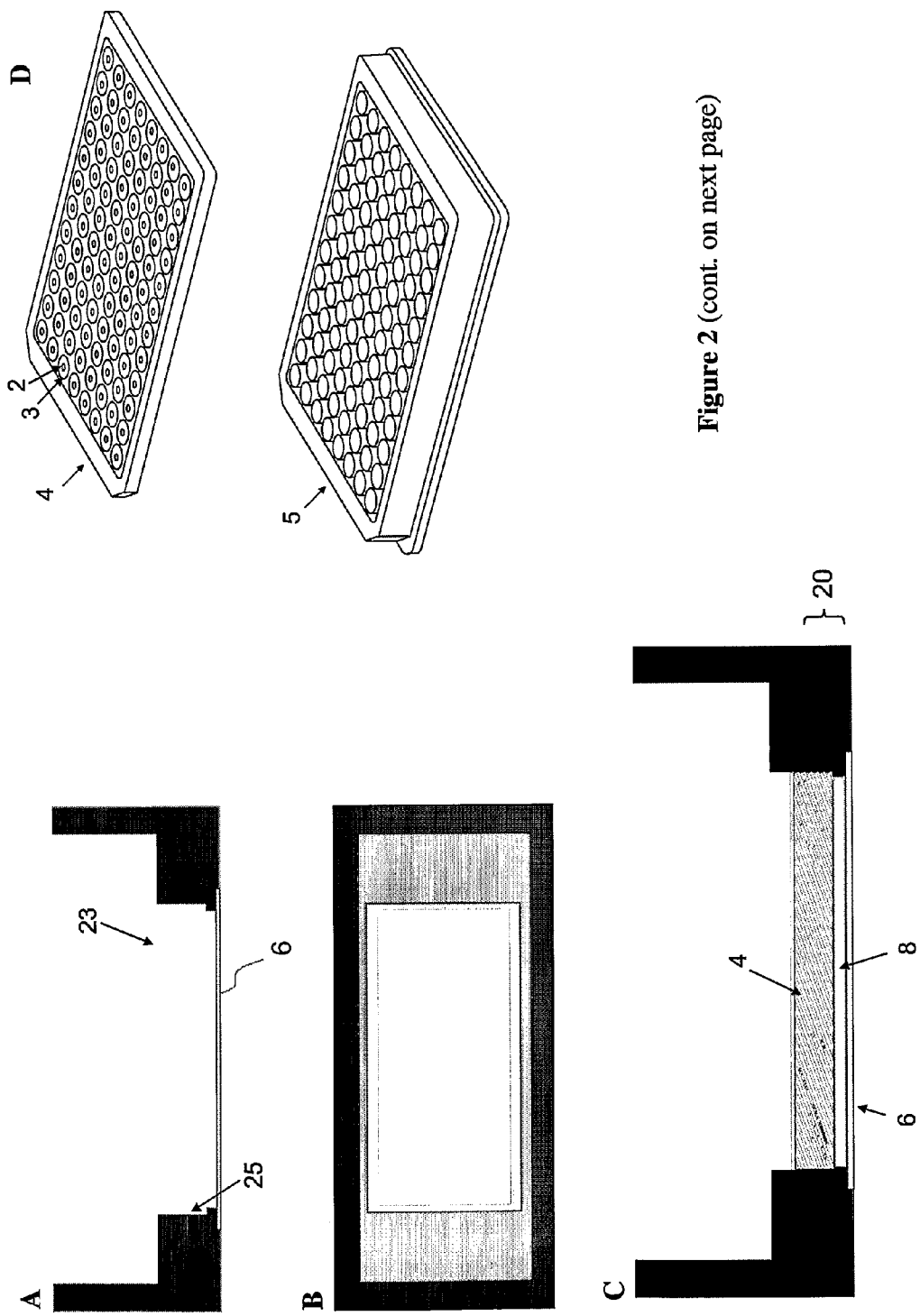
Figure 2 (cont. on next page)

1 – 200 nL     100 – 1000 μL

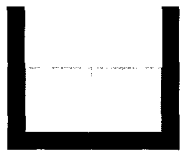
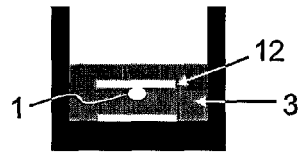
Fig. 4G
Bulk        Miniaturization
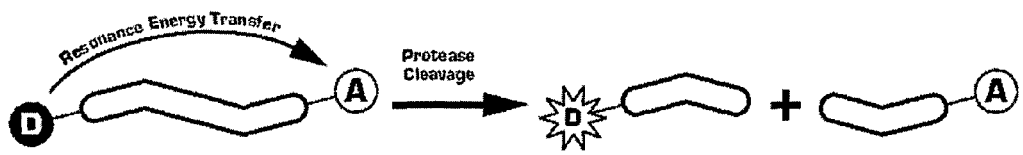
Fig. 4H
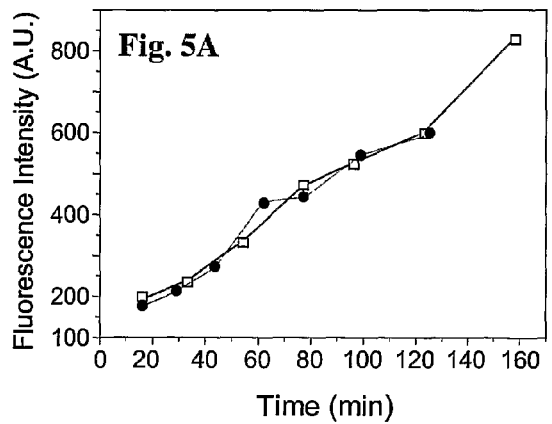
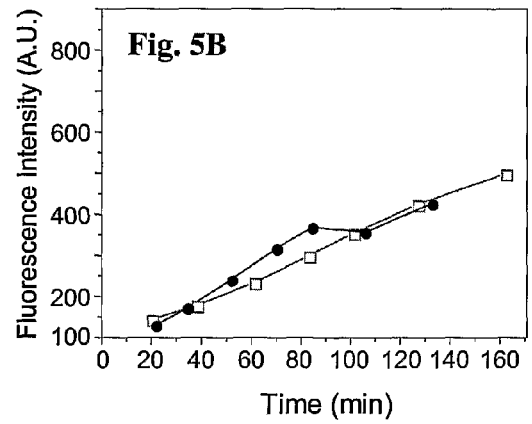
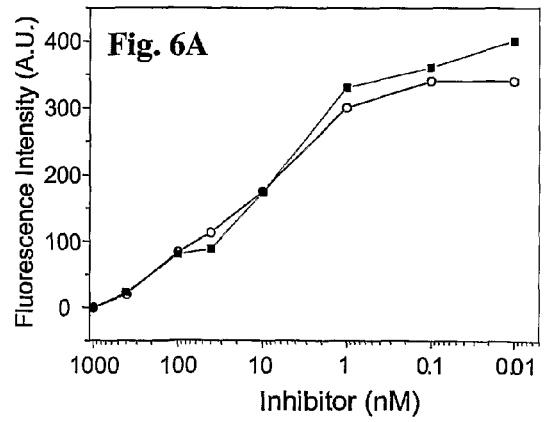
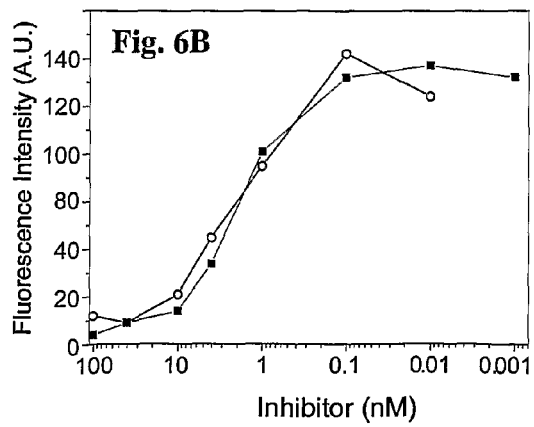

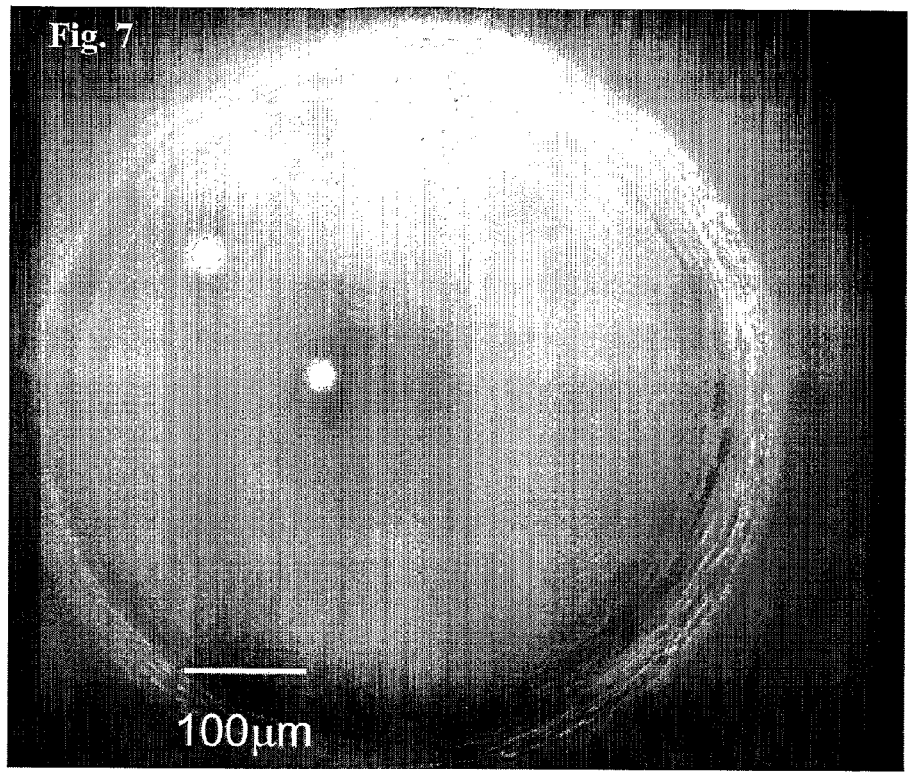
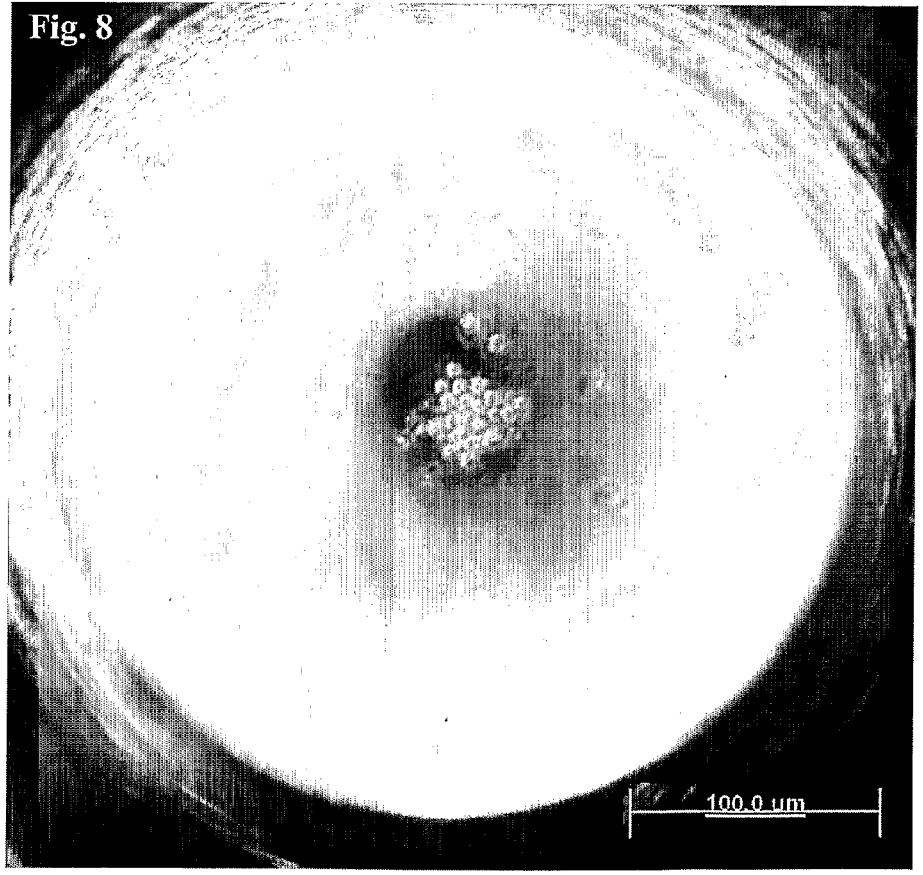

APPARATUS FOR PERFORMING A REACTION IN A DROPLET AND METHOD OF USING THE SAME

FIELD OF THE INVENTION

The present invention relates to an apparatus and a method for processing a biological and/or chemical sample in a liquid droplet.

BACKGROUND OF THE INVENTION

Miniaturization continues to play a role of an enabling technology in bioinstrumentation by offering key advantages to research in life sciences and pharmaceuticals. Most importantly, it allows significant reduction of research expense by decreasing the consumption of expensive reagents. Furthermore, it enables the study of proteins and compounds that are rare or too expensive to run at a bulk scale. Miniaturization of assays facilitates the increase in through-put and density of information, and can lead to better data quality and less sample variation in a series of assays.

Efforts on miniaturization in bioinstrumentation have delivered a number of revolutionary tools and opened a new venue in life science and pharmaceutical research. Notably, miniaturization enabled large-scale analysis of biological samples at a lower cost, faster speed and simpler operation, and brought about the era of '-omics'. A well-known example of a miniaturized device is a DNA microarray. It allows for a large-scale parallel analysis or reaction of samples in a relatively short time and at a low cost. Efforts are currently taken to miniaturize the commonly used multiwell plate (also called "Micro-Titer Plate®"). By means of automation of sample handling high-throughput screening can be performed. It has been proposed to extend the respective miniaturization approach by disposing drops of cells onto a substrate, so that they are substantially arranged in a monolayer (cf. international application WO 2004/111610).

Another example of a miniaturized device is a lab-on-a-chip microfluidic device. Such a lab-on-a-chip device additionally provides fluid manipulation functions, thus allowing mixing, separation, reaction, analysis, detection and measurement processes. Respective chips may also be combined with the multiwell plate approach, which has for example been carried out in establishing a three-dimensional cell culture system (Torisawa, Y. et al., Biomaterials (2005) 26, 2165-2172, Japanese patent application JP 2005095058). As a further approach in miniaturization, the use of microdroplets in an electric field has been suggested for microscale introduction and mixing of material (Velev, O. D. et al., Nature (2003) 426, 515-516). These microdroplets become charged and move in an electric field by a phenomenon known to those skilled in the art as dielectrophoresis (DEP). In another approach, it has been suggested to apply the principles used in magnetic or optical storage media, by placing cells such as droplets on the non-wettable surface of e.g. a rotating disk (U.S. Pat. No. 6,121,048). Yet a further miniaturization approach is the use of microbeads, e.g. in combinatorial chemistry or on-bead assays. Microbeads can be automatically sorted and dispensed based on their properties such as optical density or fluorescent characteristics.

In order to minimize protein adsorption at the solid-water interface, usually a surface treatment such as a coating is employed. However, achieving reproducibility, consistency and uniformity of differential surface coatings and establishing good quality control are a continuous challenge in the production environment.

Protein adsorption is furthermore not only a problem occurring at solid-water, but also at air-water and, where applicable, oil-water interfaces. Recently, Roach et al. (Anal. Chem. (2005), 77, 785) characterized nonspecific protein adsorption at the aqueous-perfluorocarbon interface, as well as ways to control adsorption. In their work, an aqueous droplet of protein and enzyme was encapsulated by perfluorocarbon liquid containing perfluorocarbon-ethylene glycol surfactants. The perfluorocarbon liquid-aqueous interface minimized non-specific adsorption of fibrinogen and bovine serum albumin at the interface. The activities of ribonuclease A and alkaline phosphatase at nanoliter scale surrounded by the perfluorocarbon-aqueous interface were identical to those at the bulk scale. The interface between perfluorocarbon liquid and aqueous solution, particularly in embodiments where for instance a perfluorocarbon-ethylene glycol surfactant is present, provides a biocompatible surface in addition to minimizing evaporation of the aqueous solution. Perfluorocarbon liquid is known to provide one of the most biocompatible interfaces among water-immiscible liquids.

A further problem in the use of microdevices, particularly during incubation at for instance 37° C., prolonged storage and extended sample preparation using for instance large numbers of multiwell plates for screening purposes is evaporation. Currently used means to overcome this problem are the use of multiwell-plate covers or seal-strips, stacking, the use of closed micochips and the optimization of assay protocols in order to minimize waiting time. Evaporation is of particular practical concern, since it can falsify data if it occurs unevenly across multiwell plates.

Additionally, the freedom and flexibility of liquid handling for addition and mixing of different reagents become limited upon miniaturization. The most common platform for miniaturization is a lab-on-a-chip. In this platform, a reagent is injected through an orifice and transported to a specific chamber or area through a rather long channel. In a lab-on-a-chip device, the fluidic circuit generally needs to be preprogrammed accordingly in advance, and it is inconvenient, if not infeasible, to add a specific reagent to a specific position as needed. In an open-well design, this kind of operation can however be performed by simply placing a dispenser above the desired position and dispensing the reagent. It is therefore desirable to be endued with an open-well design in which it is simple and straightforward to configure dispensing and mixing of reagents in a chip.

Accordingly it is an object of the present invention to provide an apparatus and a method for processing a chemical and/or biological sample which avoids the above discussed disadvantages of a multiwell-plate and lab-on-a-chip device.

SUMMARY OF THE INVENTION

In one aspect the present invention provides an apparatus for processing a biological and/or chemical sample in a liquid droplet. The apparatus includes a processing compartment, a base and at least one circumferential wall. The processing compartment is defined by at least a part of the base of the apparatus, at least a part of the at least one circumferential wall and an inlet member. The inlet member is located on a top of the processing compartment. The inlet member includes at least one droplet inlet channel. The droplet inlet channel is extending through the inlet member. The droplet inlet channel includes a contraction between the inlet opening of the inlet member to the environment and the outlet opening of the inlet member to the processing compartment.

In a further aspect the invention provides a method of processing a biological and/or chemical sample in a liquid droplet. The method includes providing an apparatus. The apparatus includes a processing compartment, a base and at least one circumferential wall. The processing compartment is defined by at least a part of the base of the apparatus, at least a part of the at least one circumferential wall and an inlet member. The inlet member is located on a top of the processing compartment. The inlet member includes at least one droplet inlet channel. The droplet inlet channel is extending through the inlet member. The droplet inlet channel includes a contraction between the inlet opening of the droplet inlet channel to the environment and the outlet opening of the droplet inlet channel to the processing compartment. Providing the apparatus may include providing a device that includes a reservoir that is capable of accommodating an inlet member, providing a respective inlet member, and disposing the inlet member into the reservoir, thus forming the processing compartment of the apparatus.

The method includes also providing a medium that is immiscible with the liquid droplet. The method further includes disposing the medium into the processing compartment of the apparatus provided, such that the contraction included in the inlet member is immersed in the medium. The method also includes disposing the droplet into the droplet inlet channel of the inlet member, such that the liquid droplet is located below the contraction of the at least one droplet inlet channel. The method also includes performing a process on the biological and/or chemical sample in the droplet.

BRIEF DESCRIPTION OF THE DRAWINGS

The invention will be better understood with reference to the detailed description when considered in conjunction with the non-limiting examples and the accompanying drawings, in which:

FIG. 5 depicts experimental data of a β-Secretase assay performed in a conventional tube (□) and using the apparatus of the present invention (●), at enzyme concentrations of 0.34 units/mL (A) and 0.17 units/mL (B).

FIG. 6 depicts experimental data of a Caspase assay performed in a conventional tube (■) (cf.

FIG. 7 depicts a photo of a 20 nl-droplet containing living cells that may be used in an apparatus of the present invention.

FIG. 8 depicts a photo of MC3T3 cells in a droplet of cell culture medium, that may be dispensed into the processing compartment by means of a nozzle (cf. also FIG. 9).

DETAILED DESCRIPTION OF THE INVENTION

Figures 1A, 1B, 1C:
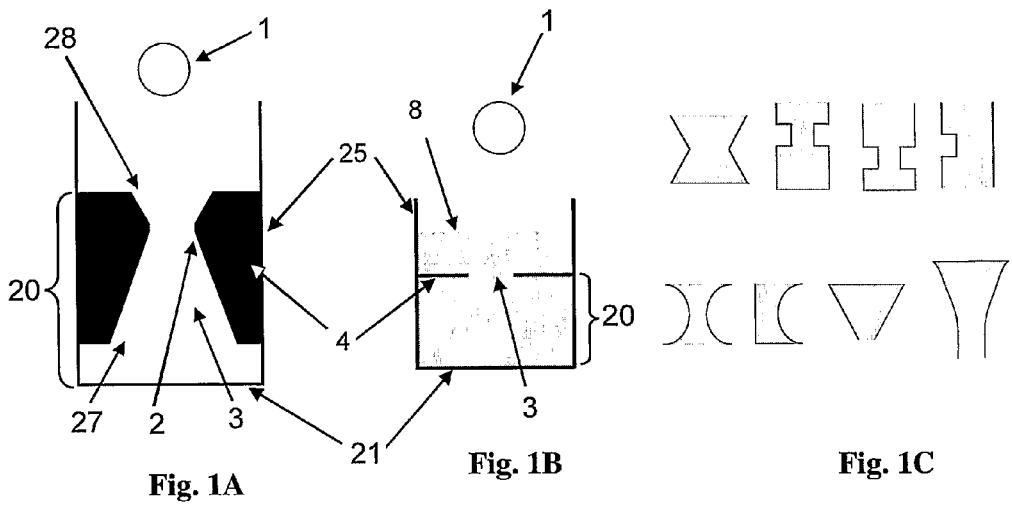
FIG. 1 depicts embodiments of an apparatus according to the present invention for processing a sample in a droplet (1) (A, B, D, E) and of profiles of contractions of a droplet inlet channel included therein (C).

The present invention provides an apparatus for processing a biological and/or chemical sample in a liquid droplet. The apparatus is suitable for any process, in particular a process that can be performed in a liquid in microscale (cf. below). The droplet may contain any desired liquid whether nonpolar aprotic, nonpolar protic, dipolar protic, dipolar aprotic, or an ionic liquid. It should be understood that suitable liquids will allow for the desired process to take place. Examples of nonpolar aprotic liquids include, but are not limited to, hexane, heptane, cyclohexane, benzene, toluene, pyridine, dichloromethane, chloroform, carbon tetrachloride, carbon disulfide, tetrahydrofuran, dioxane, diethyl ether, diisopropylether, ethylene glycol monobutyl ether or tetrahydrofuran. Examples of dipolar aprotic liquids are methyl ethyl ketone, methyl isobutyl ketone, acetone, cyclohexanone, ethyl acetate, isobutyl isobutyrate, ethylene glycol diacetate, dimethylformamide, acetonitrile, N,N-dimethyl acetamide, nitromethane, acetonitrile, N-methylpyrrolidone, and dimethylsulfoxide. Examples of polar protic liquids are water, methanol, ethanol, butyl alcohol, formic acid, dimethylarsinic acid [$(CH_3)_2AsO(OH)$], N,N-dimethyl-formamide, N,N-diisopropylethylamine, or chlorophenol. Examples of nonpolar protic liquids are acetic acid, tert.-butyl alcohol, phenol, cyclohexanol, or aniline. Two illustrative examples of ionic liquids are 1,3-dialkylimidazolium-tetrafluoroborates and 1,3-dialkylimidazolium-hexafluoroborates. In this conjunction it is noted that a droplet that may be used in the invention may be of any viscosity that is suitable for the desired process to be carried out. Besides being an aqueous solution of low viscosity that is typically used in enzymatic assays, the droplet may for instance also include, or consist of, highly viscous material, for instance castor oil, a molten polymer or a peptide hydrogel such as peptide hydrogels commercially available from Becton, Dickinson and Co, if used for the cultivation of cells. The droplet may, for example, also be of high viscosity if it is used for protein crystallization and thus has a high salt concentration or includes precipitation agents such as polyethylene 4000 or polyethylene 1000 which are commonly used for protein crystallization. The droplet may also contain more than one liquid. If more than one liquid is used, the liquids are generally miscible with each other in the selected ratio.

The droplet may be of any desired volume. It may for instance have a volume in the range of about 0.1 nl to about 50 μl, for instance 1 nl to about 200 nl. In typical embodiments the droplet is of a volume of below 10 μl. The skilled artisan will be aware that when using a droplet of large volume (such as e.g. 10 μl or 50 μl), the respective droplet may split into smaller droplets when contacting a medium. Where such splitting is undesired, suitable volumes for a droplet of a selected liquid can easily be determined experimentally.

The apparatus of the invention furthermore includes a base and at least one circumferential wall, generally a lateral wall. The apparatus also includes a processing compartment. The at least one circumferential wall, or a part thereof, together with the base, or a part thereof and an inlet member (cf. below) define the processing compartment and determine its shape (cf. e.g. FIGS. 1A-1E).

The processing compartment includes a part of the base and a part of the circumferential wall or walls. Both the circumferential wall(s) and the base of the apparatus may furthermore be a part of or surround other structures that may be included in the apparatus. In some embodiments at least the inner surface of a part of the circumferential wall of the apparatus provides the circumferential wall of the processing compartment—or a part thereof, while in other embodiments the entire circumferential wall of the apparatus provides the circumferential wall of the processing compartment. Likewise, in some embodiments the inner surface of a part of the base of the apparatus provides the base of the processing compartment, while in other embodiments the entire base of the apparatus provides the base of the processing compartment. Hence, the processing compartment is defined by a circumferential wall, a base and the inlet member, the latter defining a or the top of the processing compartment. In some embodiments the circumferential wall and the base of the apparatus of the invention are identical to the circumferential wall and the base of the processing compartment. In some embodiments the inner surfaces of the circumferential wall and the base of the apparatus define the circumferential wall and the base of the processing compartment. In yet further embodiments a part or parts of the circumferential wall and the base of the apparatus overlap with the circumferential wall and the base of the processing compartment. Accordingly, in a further aspect the apparatus of the invention can be defined as including a processing compartment, which is defined by a circumferential wall, a base and an inlet member, wherein the inlet member is located on a top of the processing compartment, being at least essentially opposite to the base.

The circumferential wall and the base of the apparatus, as well as the circumferential wall and the base of the processing compartment may include or consist of any desired material. Typically, those parts of the circumferential wall or walls as well as those parts of the base of the apparatus, which are surrounding the processing compartment, are solid and do not interfere with the processing of a biological and/or chemical sample that is performed or desired to be carried out therein. The circumferential wall(s) and the base of the apparatus (as well as the processing compartment) may for instance include an organic, inorganic or metallic substrate, such as plastic— for instance a perfluorocarbon polymer, a hydroperfluorocarbon polymer, glass, quartz, silicon, anodized aluminum, or stainless steel. The processing compartment may be of any desired form and volume. In some embodiments it may for example be designed or adapted to provide a volume that limits the freedom of movement of a droplet disposed therein. In such an embodiment the volume of the reservoir may for instance be of 1 nl to 500 µl, or a volume of 100 nl to 10 µl. In other embodiments the processing compartment may be designed or adapted to be capable of accommodating large quantities of droplets at the same time. In such an embodiment the volume of the processing compartment may for instance be of 0.1 ml to 500 ml, or a volume of 1 ml to 100 ml. Where a medium is filled into the processing compartment, only part of the volume of the processing compartment may be filled with the respective medium. The remainder of the processing compartment may for instance be occupied by other media, such as a fluid, for instance air or an inert gas.

As already indicated above, the processing compartment also includes an inlet member, which is located on a top of the processing compartment. The inlet member thus defines the upper end of the processing compartment (cf. also below). The inlet member is typically located opposite or essentially opposite the base. The terms "upper", "vertical", "below", "above", "on top of" and "on a top of" as used herein, refer to a position, where the apparatus of the present invention is positioned in such a way that the base is located on the ground, or where it is positioned such that the level of the base is at least essentially parallel to the level of the ground. In typical embodiments, this position reflects an orientation of the apparatus, where the inlet opening of the inlet member is facing upward, and in which the device can be placed onto a flat surface (cf. e.g. FIG. 1).

Since the inlet member is located on a top of the processing compartment, it is capable of establishing a fluid communication with the space above the processing compartment. The processing compartment is furthermore capable of being in fluid communication with the environment of the apparatus. Typically the apparatus includes an upper inlet, such as for instance an opening. This upper inlet is capable of providing a fluid communication between the processing compartment and the environment of the apparatus. Such an inlet may be used for introducing matter into the processing compartment, such as a medium or a droplet. In one embodiment the inlet is positioned and shaped to assist the positioning of a droplet when disposed into the processing compartment (cf. e.g. FIG. 1E). In this embodiment the inlet may also assist in preventing a droplet from splitting into smaller droplets when contacting a medium in the processing compartment. In some embodiments a respective inlet may be sealable, for example by means of a lid. As will become apparent below, the device and method of the invention can however conveniently be used without sealing inlets of the processing compartment.

In some embodiments the processing compartment of the apparatus is designed or adapted to accommodate a medium. In such embodiments the processing compartment is generally capable of accommodating a medium that is immiscible with a liquid (including a fluid-such as a liquid-mixture) that is contained in the droplet (cf. below). Thus the respective medium and the liquid of the droplet are incapable of mixing or attaining homogeneity when combined. In such embodiments any medium may be used in the device of the invention as long as a droplet of a desired liquid is able to enter it and to remain intact when contacting and entering the medium. The medium may for example be a fluid, such as for instance a liquid. As an illustrative example of a respective liquid, where the liquid contained in the droplet is water, a suitable immiscible liquid is octane, and vice versa. As a consequence, the droplet does not dissolve in the respective liquid, if disposed therein.

Other examples of a suitable liquid in embodiments where the liquid of the droplet is water include, but are not limited to, a mineral oil, a silicone oil, a hydrocarbon compound, a hydroperfluoro carbon compound or a perfluorocarbon compound. A perfluorocarbon (PFC) compound is a perfluorinated, i.e. a fully fluorine-substituted carbon compound. A hydroperfluorocarbon compound is a partly fluorinated hydrocarbon compound, i.e. a fluorine- and hydrogen-substituted carbon compound. Perfluorocarbon and hydroperfluorocarbon compounds consist of straight- or branched alkyl chains and/or rings, which may contain one or more unsaturated carbon-carbon bonds, as well as aromatic moieties. The chain/ring of a perfluorocarbon compound may contain heteroatoms, i.e. atoms that differ from carbon. Examples of such heteroatoms include, but are not limited to, O, N, S and Si.

Numerous perfluorocarbon and hydroperfluoro carbon compounds are known in the art. Examples of perfluorocarbon compounds include, but are not limited to, docosafluorodecane [Chemical Abstract No 307-45-9], dodecafluoropentane [CAS No 678-26-2], 1,1,1,2,2,3,3,4,4,5,5,6,6,7,7,8,8-heptadecafluoro-octane [CAS No 335-65-9], perfluorodecalin [CAS No 306-94-5], tetratriacontafluorohexadecane [CAS No 355-49-7], n-perfluorohexane, 1,1,1,2,2,3,3,6,6,7,7,8,8,8-tetradecafluoro-4-octene [CAS No 3910-82-5], 1,1,2-trihydroperfluoro-1-decene [CAS No 21652-58-4], 1,1,2-trihydroperfluoro-1-octene [CAS No 25291-17-2], 1,1,1,2,2,3,3,4,4,5,5,6,6,7,7,8,8-heptadecafluoro-decane [CAS No 77117-48-7], 1,1,1,2,2,3,3,4,4-nonafluoro-6-pentadecene [CAS No 118202-35-0], 8,8,9,9,10,10,11,11,12,12,13,13,14,14,15,15,15-heptadecafluoro-5-pentadecene [CAS No 118642-83-4], 2,2,3,3,4,4,5-heptafluorotetrahydro-5-(nonafluorobutyl)-furan [CAS No 335-36-4], and 4-[difluoro (undecafluorocyclohexyl)methyl]-2,2,3,3,5,5,6,6-octafluoro-morpholine [CAS No 132252-23-4]-, 1,1,2,2,3,3,3-heptafluoro-N,N-bis(heptafluoropropyl)-1-propanamine [CAS No 338-83-0], to name a few. Examples of hydroperfluoro carbon compounds include, but are not limited to, 2,2,3,3-tetrafluoro-hexane [CAS No 83225-48-3], 1,1,1,2,2,3,3-heptafluoropentane [CAS No 754-68-7], 1,1,1,2,2,3,3-heptafluoro-nonane [CAS No 755-89-5], 1,2,3,4,5,6-hexafluoro-cyclohexane [CAS No 22060-80-6], trifluoromethyl-benzene [CAS-No 98-08-8], 1,2,3,4-tetrafluoro-naphthalene [CAS No 711-55-7], 1,1'-oxybis[3,3,4,4,5,6,6,6-octafluoro-5-(trifluoromethyl)-hexane [CAS No 220469-12-5], to name only a few.

In some embodiments of the invention the liquid of the droplet is of lower density than the medium that is immiscible therewith. In these embodiments the respective droplet floats on the surface of the medium once disposed therein. In other embodiments of the invention the liquid of the droplet is of lower density than the medium that is immiscible therewith. In these embodiments the respective droplet sinks into the medium once disposed therein.

The inner surfaces of the circumferential wall(s) and the base of the processing compartment, in the following also commonly addressed as "the inner walls", consist in some embodiments of exactly the same material as the remaining circumferential walls and the remaining base. In other embodiments the respective material includes the same or at least similar components as the remaining circumferential walls and/or the remaining base, but for instance in different amounts or ratios. In yet other embodiments they include additional or completely different material. The inner walls of the processing compartment may possess any internal surface characteristics, as long as they allow for the accommodation of a desired medium. Where for instance an aqueous fluid is provided, the inner walls may thus be either hydrophilic or hydrophobic. Furthermore, inner walls of the processing compartment may provide different surface characteristics. Thus, some inner walls or wall-portions, may be hydrophilic, while others may be hydrophobic.

Any part of the inner walls of the reservoir may also be treated in such a way that they provide respective hydrophilic or hydrophobic surface characteristics. A respective treatment may for instance be desired in order to provide a surface that possesses altered, e.g. reduced or negligible, interactions with the liquid of a selected liquid droplet. For example the base region of the reservoir may be treated respectively. In some embodiments the inner walls of the reservoir are furthermore inert against the medium that is desired to be accommodated therein. Such embodiments allow for multiple reusing of the device. An illustrative example of a material that is inert against most corrosive media is a fluoropolymer such as fluoroethylenepropylene (FEP), polytetrafluoroethylene (PFTE, Teflon), ethylene-tetrafluoroethylene (ETFE), tetrafluoroethylene-perfluoromethylvinylether (MFA), vinylidene fluoride-hexafluoropropylene copolymer, tetrafluoroethylene-hexafluoropropylene copolymer, vinylidene fluoride-hexafluoropropylene-tetrafluoroethylene terpolymer, perfluoromethyl vinyl ether-tetrafluoroethylen copolymer, perfluoroalkoxy copolymer (PFA), poly(vinyl fluoride), polychlorotrifluoroethylene, fluorosilicones, or fluorophosphazenes.

A treatment that may be carried out to alter surface characteristics may comprise various means, such as mechanical, thermal, electrical or chemical means. As an example, the surface of plastic materials can be rendered hydrophilic via treatment with dilute hydrochloric acid or dilute nitric acid. As another example, a polydimethylsiloxane (PDMS) surface can be rendered hydrophilic by an oxidation with oxygen or air plasma. Alternatively, the surface properties of any hydrophobic surface can be rendered more hydrophilic by coating with a hydrophilic polymer or by treatment with surfactants. Examples of a chemical surface treatment include, but are not limited to exposure to hexamethyldisilazane, trimethylchlorosilane, dimethyldichlorosilane, propyltrichlorosilane, tetraethoxysilane, glycidoxypropyltrimethoxy silane, 3-aminopropyltriethoxysilane, 2-(3,4-epoxy cyclohexyl) ethyltrimethoxysilane, 3-(2,3-epoxy propoxyl) propyltrimethoxysilane, polydimethylsiloxane (PDMS), γ-(3,4-epoxycyclohexyl)ethyltrimethoxysilane, poly(methyl methacrylate) or a polymethacrylate co-polymer, urethane, polyurethane, fluoropolyacrylate, poly(methoxy polyethylene glycol methacrylate), poly(dimethyl acrylamide), poly [N-(2-hydroxypropyl)methacrylamide] (PHPMA), α-phosphorylcholine-ω-(N,N-diethyldithio-carbamyl)undecyl oligoDMAAm-oligo-STblock co-oligomer (Matsuda, T et al., Biomaterials, (2003), 24, 24, 4517-4527), poly(3,4-epoxy-1-butene), 3,4-epoxy-cyclohexylmethylmethacrylate, 2,2-bis[4-(2,3-epoxy propoxy)phenyl]propane, 3,4-epoxy-cyclohexylmethylacrylate, (3',4'-epoxycyclohexylmethyl)-3,4-epoxycyclohexyl carboxylate, di-(3,4-epoxycyclohexylmethyl)adipate, bisphenol A (2,2-bis-(p-(2,3-epoxy propoxy) phenyl)propane) or 2,3-epoxy-1-propanol.

Where it is desired to provide a hydrophobic inner wall (or wall portion) of the processing compartment, the respective wall, in particular the wall surface, may for instance include a hydrophobic material such as for instance polyethylene, polypropylene, polyester, polyestersulfone or a perfluorocarbon compound such as polytetrafluoroethylene (PFTE).

In some embodiments an inner wall or a portion of a wall of the processing compartment of the apparatus a material thus possesses such a low affinity to the liquid of a droplet that hardly any or no interaction between the surface of the inner wall and a respective droplet is detectable. As an illustrative example it may be desired to avoid an attachment of a droplet to an inner wall, for instance the base region of the processing compartment, when a droplet has been immersed into the medium that is accommodated by the processing compartment. In such embodiments an electric field, including an electrostatic field, or a magnetic field (cf. below) may be applied to immerse a droplet that is of lower density than the medium accommodated in the processing compartment. In such a case the droplet may be immersed by the electric or magnetic field as far as for instance the base region of the processing compartment. If the base region has a high affinity to the droplet, the droplet may thus stick to the base region. If the base region has no affinity to the droplet, the droplet will be forced upward by buoyancy force, after the electric/magnetic field ceases to exist. Accordingly, in some embodiments a surface, in particular the internal surface, of the base region of the processing compartment includes a material of such low affinity to the liquid of the droplet that the maximal force, which the affinity of the material is capable of exerting on the droplet in the medium, is below the buoyancy force.

In some embodiments the base of the processing compartment of the apparatus possesses a translucent region. The term "translucent" is understood to describe the property of a material to allow at least a certain percentage of radiation to pass through. In one of these embodiments the base possesses an at least substantially transparent region. As an illustrative example, a part of the base region or the entire base region may be translucent within a certain range of the electromagnetic spectrum, for example visible light, infrared light, X-ray and/or UV light. It may e.g. be transparent or essentially transparent in the range of visible light, i.e. for energy of a wavelength of about $7 \times 10^{-5}$ to about $4 \times 10^{-5}$ cm. In some embodiments the translucent (including transparent) region may assist in allowing energy, which is used for a particular process to be initiated or catalyzed or for a detection process to be performed, to enter the processing compartment. In some of these as well as in other embodiments the transparent or essentially transparent region assists in or allows for energy to leave the processing compartment, for example during a detection process. In some embodiments the respective translucent region is made of a different material than the remaining processing compartment. Examples of suitable material for a transparent region include, but are not limited to, glass or plastic material. Suitable plastic materials for the generation of a translucent or a transparent region include, but are not limited to, polymethylmeacrylates (e.g. polymethyl-methacrylate (PMMA) or carbazole based methacrylates and dimethacrylates), polystyrene, polycarbonate, and polycyclic olefins. A further illustrative example of a material that is additionally suitable for the generation of a translucent region is fluoro-ethylen-propylen (FEP).

The circumferential wall or walls of the processing compartment may be of any geometry and number. As an illustrative example the apparatus may contain a (vertically) straight lateral wall. This circumferential/lateral wall may for instance be a cylindrical wall surrounding the processing compartment. As a further example of a straight circumferential wall the apparatus may contain one lateral wall of horseshoe shape and one flat lateral wall, connected with each other via edges. As yet a further example the apparatus may contain 3, 4, 5, or more flat or rounded circumferential walls connected via edges. The design, number and arrangement of the circumferential walls, as well as the design of the base, may for example be selected with a view to a device that is located or to be placed inside the processing compartment.

Such a device, which is included in the processing compartment, is an inlet member (cf. e.g. FIG. 1). The inlet member assists in fixing a droplet in the processing compartment (cf. below, cf. e.g. FIGS. 4A-4E for an illustration). In some embodiments the inlet member is an integral part of the apparatus. It may for instance project from a circumferential wall or the base of the processing compartment. In other embodiments the inlet member is removable from the processing compartment. In one of these embodiments the inlet member is removable from the apparatus. The inlet member may be of any shape and any material. It may for instance be a plate, a brick or a disk (cf. also below). Examples of materials, which may be included in such an inlet member, include, but are not limited to, a metal, quartz, glass, silicone, a plastic, a polymer, a ceramic, an insulator, a semiconductor, organic material, inorganic material and composites thereof. Besides including the droplet inlet channel, the inlet member may include other devices or components such as for instance a barcode-area or a handle.

Like the base of the apparatus, the surfaces of the inlet member, including the surfaces of the droplet inlet channel, may include the same and/or different material as the remainder of the inlet member. Furthermore, the surfaces of the inlet member may possess any surface characteristics, as long as they allow for the accommodation of the inlet member in a desired medium (cf. above). Any part of the surface of the inlet member may also be treated in such a way that it provides respective hydrophilic or hydrophobic surface characteristics (cf. above).

In some embodiments a surface or a portion of the inlet member includes a material thus possesses such a low affinity to the liquid of a droplet that hardly any or no interaction between the surface of the inlet member and a respective droplet is detectable. As an illustrative example it may be desired to avoid an attachment of a droplet to an inlet member, for instance the droplet inlet channel, when a droplet has been immersed into the medium that is accommodated by the processing compartment. In such a case the droplet may be immersed into the medium by gravity and thereafter contact the inlet member. By means of for instance an electric field (including an electrostatic field) or a magnetic filed (cf. also below) the droplet may furthermore be forced through the droplet inlet channel of the inlet member. In such and other embodiments it may be desired to avoid significant interactions between the droplet and the surface of the droplet inlet channel, for instance in order to assist the transfer of the droplet through the contraction of the droplet inlet channel. Accordingly, in some embodiments the surface of the droplet inlet channel, or a part thereof, includes a material of such low affinity to the liquid of the droplet that the maximal force, which the affinity of the material is capable of exerting on the droplet in the medium, is below the force exerted by the electric/magnetic field. In other embodiments the surface of the droplet inlet channel, or a part thereof, includes a material of such low affinity to the liquid of the droplet that the maximal force, which the affinity of the material is capable of exerting on the droplet in the medium, is below the force exerted by gravity.

In another case an electric or magnetic field may be applied to immerse a droplet that is of lower density than the medium accommodated in the processing compartment. If the base region has a high affinity to the droplet, the droplet may thus stick to the base region. If the base region has no affinity to the droplet, the droplet will be forced upward by buoyancy force, after the electric/magnetic field ceases to exist. Accordingly, in some embodiments the internal surface of the base region of the processing compartment includes a material of such low affinity to the liquid of the droplet that the maximal force, which the affinity of the material is capable of exerting on said droplet in the medium, is below the buoyancy force.

Where desired, a surface of the inlet member may include a material that is inert against most corrosive media and at the same time is of such low affinity to the liquid of the droplet that the maximal force, which the affinity of the material is capable of exerting on the droplet in said medium, is below the buoyancy force. An illustrative example of such a material is a fluoropolymer such as fluoroethylenepropylene (FEP), polytetrafluoroethylene (PFTE) ethylene-tetrafluoroethylene (ETFE), tetrafluoroethylene-perfluomethylvinylether (MFA), or perfluoroalkoxy copolymer (PFA). In one embodiment of the invention, the surface of the droplet inlet channel includes such a material.

In some embodiments the processing compartment of the apparatus is capable of accommodating a respective plate in its entirety (cf. e.g. FIG. 2C). Such embodiments may for instance be selected where the processing compartment is desired to accommodate a liquid. Accordingly, in such embodiments the plate will be entirely immersed in a medium, once the processing compartment accommodates the latter. In some of these embodiments the processing compartment provides a separate inlet for a respective plate to be placed into the processing compartment. Some embodiments may allow for a respective plate to be immersed in several micro-devices at the same time, by for instance providing corresponding sealable openings in each device. In one embodiment a respective plate may be moved from one device to another one. In this context it will be understood that the device and method of the present invention do generally not require a transfer of a sample from one device to another.

The inlet member of the apparatus of the invention includes at least one droplet inlet channel. The droplet inlet channel is extending through the inlet member. The droplet inlet channel has an inlet opening and an outlet opening (cf. e.g. FIG. 1A). The outlet opening is an opening to the processing compartment, the inlet opening is an opening to the space above the inlet member. Above or on a top of the inlet member there may in some embodiments be a further interior of the apparatus. In other embodiments the inlet member may form the top of the apparatus. In such an embodiment the inlet opening may thus be an opening to the environment of the apparatus. In all these embodiments the processing compartment is in fluid communication with the environment via the inlet of the inlet member.

Furthermore, the droplet inlet channel includes a contraction between the inlet opening and an outlet opening. Since the inlet member forms the upper end of the processing compartment, the droplet inlet channel is able to provide a communication means between the processing compartment and the ambience located above the same. Accordingly, the lower part of the droplet inlet channel, i.e. the part which extends from the contraction downward, forms part of the processing compartment. Where the droplet inlet channel includes more than one contraction, the respective contraction forming the upper end of the processing compartment may be defined as the contraction with the smallest diameter available for a liquid droplet to pass.

The contraction has a profile in the plane parallel to the plane of the base region of the processing compartment. Generally this plane is at least essentially parallel to the plane of its with, and furthermore it is generally at least essentially parallel to the upper surface of a medium in the processing compartment that is immiscible with the liquid droplet. In this plane parallel to the plane of the base region the diameter of the contraction may be of any profile, for instance round, square, triangular or of the shape of any oligoedron, as long as it provides an opening that allows a fluid communication between the processing compartment and the environment. Likewise, in the plane parallel to the plane of the base region, the profile of the at least one droplet inlet channel may be of any geometry (cf. also below). The profile of the droplet inlet channel may in the respective plane for instance be of at least one of the shape an hourglass, a concave semicircle, V-shape, a triangle, a rectangle, a square, any oligoedron, and any combination thereof. In some embodiments the opening defined by the contraction of the droplet inlet channel is selected to be of a diameter that is smaller than the diameter that the liquid droplet has in the immiscible medium (cf. also below). In some of these embodiments the diameter that is, whether theoretically or in a chosen embodiment, available for any liquid droplet to pass, is smaller than the diameter of the specific liquid droplet used has in the immiscible medium. The exact diameter, or diameter available for a (i.e. any) liquid droplet to pass, of the contraction in such embodiments accordingly depends on the selected medium and the selected liquid droplet under the desired temperature and pressure conditions. In particular the diameter depends on the resulting size of the liquid droplet once dispensed into the medium in the processing compartment. As an illustrative example, the diameter of the contraction that is available for the droplet to pass, may be selected in a range between 100 µm and 10 mm, such as for instance in a range between 300 µm and 2 mm.

Typically the contraction of the droplet inlet channel is capable of preventing a droplet, which includes the sample, from spontaneously passing through the droplet inlet channel. The skilled artisan will be aware that, depending on the liquid of the droplet used and the media that is included in the processing compartment, such spontaneous movement of a droplet may for instance be driven by gravitational or buoyant force.

Once the processing compartment accommodates an inlet member and a certain amount of medium, the contraction is immersed in the medium. The diameter of the contraction may be of any profile in the plane parallel to the base (i.e. generally also parallel to the surface of the liquid). Examples of respective profiles include, but are not limited to, the shape of a circle, a semicircle, an egg, V-shaped, 1-shape, U-shaped, lanceolate (shaped like a lance point), trapezium shaped, the shape of an hour glass, a triangle, a rectangle, a square, any oligoedron or any combination thereof. The contraction may furthermore be of any thickness in the plane perpendicular to the base. As an illustrative example, it may be of a thickness in the range of about 100 µm to 10 cm, for instance in the range of about 300 µm to 5 mm.

The contraction is typically of smaller diameter than the diameter which the droplet has in the medium. It thus requires a certain amount of force to pass a droplet through the contraction. Once a droplet has been forced through the contraction, it remains trapped there under or there above since it is bigger than the contraction. Buoyancy or gravitational forces are not sufficient to force the droplet back. At the same time the contraction may also serve as a selective filter in embodiments where droplets are formed with a diameter that is subject to a certain degree of variability. Droplets of a larger or smaller diameter than the expected value in the immiscible liquid used, will either pass through the contraction without additional force being applied or not be able to pass through the contraction.

The contraction may for instance be a neck or a hole in the droplet inlet channel or be included therein. The droplet inlet channel may be of any profile in the plane perpendicular to the base of the apparatus (supra). Such a profile may be symmetrical or asymmetrical. It may for instance be derived from the shape of a cylinder that is of nonuniform diameter. Examples of respective profiles include, but are not limited to, the shape of a circle, a concave semicircle (plano-concave), egg-shape, V-shaped, C-shaped, D-shaped, I-shaped, lanceolate, trapezium shaped, the shape of a concave semicircle (plano-concave), a triangle, a rectangle, a square, or any oligoedron. FIG. 1B depicts a few illustrative examples of suitable profiles the droplet inlet channel. In some embodiments the diameter available for a droplet to pass through may narrow with increasing distance from the surface of the liquid that is immiscible with the droplet. A respective droplet inlet channel may for instance have a V-shaped profile.

In one of these embodiments the contraction, which is of a diameter smaller than the diameter which the droplet has in the liquid, is located at the bottom of the droplet inlet channel. A respective profile of a droplet inlet channel may be desired in order to guide a droplet toward a contraction.

In some embodiments the diameter of a droplet inlet channel available for a droplet to pass through may increase with increasing distance from the surface of the liquid that is immiscible with the droplet. A respective droplet inlet channel may for instance have a pyramid-shaped or a cone-shaped (Δ-shaped) profile.

In one of these embodiments the contraction of a diameter smaller than the diameter which the droplet has in the liquid is comprised at the top of a droplet inlet channel. A respective profile of a droplet inlet channel may be desired in order to secure a droplet at a position directly under a contraction. Securing a droplet in a certain position may for example be desired where a detection or radiation of the droplet etc. are to be carried out. It may for instance also be desired to assist identification purposes in embodiments where several different droplets are used.

In some embodiments the diameter of a droplet inlet channel available for a droplet to pass through may decrease with increasing distance from the inlet opening up to a certain point. Thereafter the available diameter of a droplet inlet channel may increase again with increasing distance from the from the inlet opening, i.e. with decreasing distance to the outlet opening. As an illustrative example, the droplet inlet channel may be of the profile of an hourglass in the plane perpendicular to the surface of the liquid. The first six profiles depicted in FIG. 1B are further examples of respective profiles of such a droplet inlet channel. In one of these embodiments the contraction of a diameter smaller than the diameter which the droplet has in the liquid is comprised within the droplet inlet channel as described above, for example in the centre or close to the centre of the droplet inlet channel. In a respective embodiment the contraction may serve as a bottleneck. Such a bottleneck may serve in blocking a droplet from passing without the action of additional external force, trapping a droplet once it has passed through it and fixing a droplet due to the action of gravitational or buoyancy force.

In some embodiments of the invention, the apparatus provides a plurality of inlet openings and/or contractions, for example as described above. Any arrangement of inlet openings and/or contractions may be chosen in such an embodiment. In one embodiment all inlet openings are identical (cf. e.g. FIG. 1D or FIGS. 4A-4E). In such an embodiment several droplets of the same diameter and for instance also of the same liquid may be used with the device at the same time. In another embodiment several droplet inlet channels may be provided that possess an identical profile in a level perpendicular to the base of the apparatus, which are however of a different diameter available for a droplet to pass. As an illustrative example, the contraction of these droplet inlet channels may provide a different diameter available for a droplet to pass. In yet another embodiment there are contractions provided that are located differently, e.g. within droplet inlet channels of different profile, and that posses a different diameter available for a droplet. In each of these embodiments all or several contractions may be located within identical material or within different material (cf. below).

In some embodiments the droplet inlet channel is a through-hole of a plate, a brick or a disk, or a part thereof. A respective plate, brick or disk may be removable from the micro-device. Such a module may be of any desired form. It may thus as an example match the microtitre plate (MTP) format, where a compatibility to existing laboratory equipment is desired. As an illustrative example, the inlet openings of inlet channels of a suitable plate may be located where on a conventional 48-, 96-, 384-, 1536- or 3456 well plate the respective wells are located (see FIG. 2D for an example).

In a respective embodiment an exchange of a plate, brick or disk may provide for instance one droplet inlet channel or several droplet inlet channel of a selected diameter. An exchange of a plate, brick or disk may for example also provide a material that possesses minimal interaction with a liquid of a selected droplet, or provide a material that is treated to show no or minimal interaction with the liquid of a selected droplet (cf. below).

In some embodiments the apparatus has a thermostatic device or a Peltier heater incorporated therein to influence (by way of acting as a catalyst, for example) the processing of the chemical or biological sample by varying the temperature. In this regard, the thermostatic device or Peltier heater may act as a heating means, a cooling means or both. Accordingly, the heating or cooling means may be, but is not limited to, a Peltier heater attached to the surface or surfaces of the processing compartment, or a heating or cooling coil wound around the circumference of the processing compartment, for example to provide for uniform temperature distribution.

The present invention furthermore provides a method of processing a biological and/or chemical sample in a liquid droplet. Any process may be performed that can be performed in a liquid droplet. It is understood that further liquid droplets may be added in order to be able to perform a desired process. Examples of a process that may be performed include, but are not limited to, a physical detection of a compound that is included in the sample, a chemical reaction, a cell lysis, an extraction of a molecule from an organism or a part of an organism, a release of a molecule from an organism, and any combination thereof. Examples of a physical detection include, but are not limited to, spectroscopic, photochemical, photometric, fluorometric, radiological, or thermodynamic means and include for instance the use of photoactive, fluorescent, radioactive or enzymatic labels. Examples of a chemical reaction include, but are not limited to, a protein synthesis, a nucleic acid synthesis, a peptide synthesis, an enzymatic degradation, an interaction with a binding molecule, and any combination thereof.

When used for processing a sample, the droplet may be subjected to an energy source for particular processes to be initiated or catalyzed. Examples of energy that may be applied, include, but are not limited to, microwave or photolytic energy. The apparatus may include a certain region of a circumferential wall or base of the processing compartment that allows energy to enter and/or leave the processing compartment. In some of these embodiments the apparatus of the invention includes translucent or at least essentially transparent regions, such as a circumferential wall, or a part thereof, or the base, or a part thereof, of the processing compartment.

For some processes additional droplets may be employed, that include different material, such as e.g. reactants. Such additional droplets may for instance be merged with the droplet that includes the sample. In some embodiments, the process to be performed is the detection of an analyte. Such a process may include one or more reactions. The analyte may for instance be the sample included in the liquid droplet. The selection of reaction(s) to be carried out in such embodiments depends on the type of analyte to be detected, taking into account what are the characteristics of the analyte which would allow for its detection.

An illustrative example of reactions that may be included in a process performed in the droplet are binding reactions between an analyte that is targeted for detection and an indicator compound which provides a detectable signal to indicate positive detection of the analyte. Examples include for instance immunochemical reactions such as an Enzyme-Linked Immunosorbent Assay (ELISA), which is well known to the person skilled in the art. An assay of a respective binding reaction may also include fluorescent polarization (FP), fluoresence resonance energy transfer (FRET), fluorescence quenching or enhancement, fluorescence correlation spectroscopy (FCS), fluorescence intensity distribution analysis (FIDA), or fluorescence cross-correlation spectroscopy (FCCS). In the case of FRET, the binding partners typically need to be labeled to allow detection, for example by means of a mutant of alkylguanine-DNA alkyl transferase such as the SNAP tag (cf. Schwab, M. et al., Genetic Engineering News (2005), 25, 21). An illustrative example of a means of using FRET is a β-Secretase FRET assay, where a substrate of a peptide linked with a fluorophore and a quencher at each end becomes fluorescent upon its cleavage by the enzyme β-Secretase. In the case of FP, a fluorophore typically needs to be attached to one of the binding partners, which then forms the so called tracer. FCCS allows for a simultaneous monitoring of single- and double-labeled matter and does not require close proximity of two binding partners for their detection. Other examples include enzymatic reactions, which rely on the generation or consumption of molecules with a characteristic fluorescence or absorbance. Such reactions are well known to the person skilled in the art and involve for instance a redox change of molecules such as Nicotinamide Adenine Dinucleotide (NAD/NADH). A further well known example is a polymerase chain reaction, for instance accompanied by real time detection in the presence of a dye such as SYBR Green, which emits a fluorescence signal only when bound to double-stranded nucleic acids. Yet another example is a binding reaction between a targeted DNA sequence and its complementary DNA or fragment labeled with a fluorophore, whereby a fluorescent signal is produced if the test sample contains the target DNA sequence. As a further example, imaging of a specific molecules of interest may also be carried out by anti-Stokes Raman scattering (CARS) microscopy.

Respective reactions may provide qualitative or quantitative data which provide a colorimetric, fluorometric or luminescent result relating to an analyte present in the droplet. If a colorimetric result is desired, for example for the detection of a protein analyte, suitable dyes may be used to stain any protein present in the fluid sample. An example of a usable dye can be obtained from sulfo-rhodamine B (SRB) dissolved in acetic acid. Where a fluorometric result is desired, fluorescent dyes may be used. The fluorometric result can also be derived from fluorescence provided by either the binding of a fluorophore directly to a targeted analyte, or the binding of a fluorophore-labeled compound to the targeted analyte. As an illustrative example, amino or thio groups of an antibody directed to an analyte may be covalently linked to a small organic molecule such as Cy5, Cy7 or Dy647, or to a fluorescent protein such as allophycocyanin (APC). As a further illustrative example, the analyte may be a construct of an intracellular protein and green fluorescent protein (GFP), expressed in a cell. In a further embodiment, a probe that is bound with at least one fluorophore, enzyme, or component of a binding complex is used for the detection of the analyte.

The present method can be carried out to process samples from biological or non-biological material. Examples of non-biological material include, but are not limited to, synthetic organic or inorganic compounds, organic chemical compositions, inorganic chemical compositions, combinatory chemistry products, drug candidate molecules, drug molecules, drug metabolites, and any combinations thereof. Examples of biological material include, but are not limited to, nucleotides, polynucleotides, nucleic acids, amino acids, peptides, polypeptides, proteins, biochemical compositions, lipids, carbohydrates, cells, microorganisms and any combinations thereof.

Examples of nucleic acids are DNA or amplified products from the processing of nucleic acids for genetic fingerprinting, e.g. PCR. Examples of microorganisms include for instance pathogens such as bacteria or virus, or cancerous cells. Such analytes can originate from a large variety of sources. Fluid samples that may be analysed using the present method include biological samples derived from plant material and animal tissue (e.g. insects, fish, birds, cats, livestock, domesticated animals and human beings), as well as blood, urine, sperm, stool samples obtained from such animals. Biological tissue of not only living animals, but also of animal carcasses or human cadavers can be analysed, for example, to carry out post mortem tissue biopsy or for identification purposes, for instance. In other embodiments, fluid samples may be water that is obtained from non-living sources such as from the sea, lakes, reservoirs, or industrial water to determine the presence of a targeted bacteria, pollutant, element or compound. Further embodiments include, but are not limited to, dissolved liquids or suspensions of solids (such as microfluids) and ionic liquids. In yet another embodiment, quantitative data relating to the analyte is used to determine a property of the fluid sample, including analyte concentration in the fluid sample, reaction kinetic constants, analyte purity and analyte heterogeneity.

As an illustrative example, a bacteria, virus, or DNA sequence may be detected using the present invention for identifying a disease state. Diseases which can be detected include, but are not limited to, communicable diseases such as Severe Acute Respiratory Syndrome (SARS), Hepatitis A, B and C, HIV/AIDS, malaria, polio, tuberculosis and influenza; congenital conditions that can be detected pre-natally (e.g. via the detection of chromosomal abnormalities) such as sickle cell anaemia, heart malformations such as atrial septal defect, supravalvular aortic stenosis, cardiomyopathy, Down's syndrome, clubfoot, polydactyl), syndactyl), atropic fingers, lobster claw hands and feet, etc. The present method is also suitable for the detection and screening for cancer.

In other embodiments the method of the present invention may be employed for the detection, reaction (including a binding reaction to a biological cell or a part thereof), synthesis, or any combination thereof, of one or more pharmaceutical compounds, such as drugs. A synthesis of a compound, such as a pharmaceutical compound, may for example be performed as a solid-phase reaction on derivatised beads. Pharmaceutical compounds may for example be used in form of a library. Examples of such libraries are collections of various small organic molecules, chemically synthesized as model compounds, or nucleic acid molecules containing a large number of sequence variants. As an example, each compound of such a library may be disposed into one droplet. Such droplets may be provided in an automated way by commercially available machines, which are well known to those skilled in the art. The method of the invention may for instance be used for drug screening or for determining the presence of a drug in a urine or blood sample.

In yet another embodiment the method of the present invention may be used for protein crystallization. As an illustrative example, an array of droplets containing proteins and different types of buffers and additives in a chip may easily be. Standard requirements in the art for an optimal protein crystallization system include: (1) miniaturization for cost saving of expensive proteins, (2) flexibility of varying the crystallization solution composition in order to test a wide range of conditions in each trial, and (3) control of evaporation rate, so that evaporation happens extremely slowly over a period of up to 6 months. The present invention is able to satisfy all these requirements. The size of a droplet dispensed is merely limited by the dispenser used, and can be as small as 100 pL with commercially available technology. Each droplet of an exemplary array may be defined as a reactor. The reactor composition can be easily varied by programming the addition of a different solution to each droplet. Where for example a crystallisation solution of a protein needs to be prepared with two different additives in all possible combination of the components, the method of the invention can easily be applied. Where the target total reactor volume is 1 nL and the smallest dispensing unit is 0.2 nL, then the system can provide a total of 20 different compositions by simple programming the operation. The evaporation can be easily controlled (standard procedures, cf. also supra). At the level of 1 nL, the droplet evaporates within 1 day in perfluorocarbon liquid currently used in the art. In embodiments where the medium in the processing compartment is a perfluorocarbon liquid, and the perfluorocarbon liquid is completely covered with water (i.e. at the top, cf. also below), droplet evaporation is negligible. Accordingly, by controlling the relative humidity and the amount of water present in the perfluorocarbon liquid, the droplet evaporation rate can be adjusted as desired.

In yet a further embodiment the method of the present invention may be used for handling living cells, such as for instance performing whole-cell assays. It has previously been reported that dispensing living cells by means of reagent dispensing robots does not affect cell viability and that the cells can subsequently be grown in a 3456-well plate (Mere, L. et al., Drug Discovery Today (1999) 4, 363-369). Examples of whole-cell assays include the detection of the level of an intracellular molecule (e.g. cyclic adenosine monophosphate) or of the activity of an intracellular molecule (e.g. an enzyme such as a caspase), the determination of binding sites on the cell surface for a selected molecule, the determination of the complex formation of a molecule with such binding sites on the cell surface (e.g. as a displacement-binding assay, including a scintillation proximity assay), or the detection of an analyte in a sample in a reporter-gene-based assay. Adherent cell assays can be handled in droplets without any direct contact with a solid substrate where desired. As an example, a droplet may contain a 3-dimensional matrix material, which can function as a physical support for cell adherence. As another example, a droplet may contain particles that provide physical support for adherent cells (cf. e.g. FIG. 12).

The method includes providing an apparatus that comprises a processing compartment, defined by a base, at least one circumferential wall and an inlet member, as described above. Providing the apparatus may include providing a device that includes a reservoir that is capable of accommodating an inlet member, such as for instance a plate, a brick or a disk. In such cases the method may further include providing a respective inlet member. As described above, the surfaces of the inlet member may possess any surface characteristics, as long as they allow for a desired reaction to occur. In cases where the method includes providing a device that includes a reservoir that is capable of accommodating an inlet member, the method further includes disposing the inlet member into the reservoir, thus forming the processing compartment of the apparatus described above. The circumferential wall of the reservoir, which forms the processing compartment once the inlet member is provided therein, is in some embodiments designed or adapted to support the inlet member.

As an example, the circumferential wall of the apparatus may be extending into the interior of the processing compartment, thereby forming a step, by which the inlet member can be supported. In such embodiments the step may be designed or located to provide a distance between to the base that prevents direct contact between the base and the inlet member. Such a space may thus contribute to, or define, the height of the processing compartment. Accordingly, in such embodiments the processing compartment includes a space between the base and at least a part of the inlet member. FIG. 2A depicts an example of a respective circumferential wall that is designed or adapted to support a biochip by means of a step (see also FIG. 2B). Once the biochip is inserted into the reservoir (cf. e.g. FIG. 2G) and supported by the circumferential wall, the processing compartment is assembled (see FIG. 2C). In other embodiments the circumferential wall of the reservoir is designed or adapted to support the inlet member without providing a distance between the base and the inlet member. In some of these embodiments a space within, or a part of, the processing compartment may be separated from the remaining processing compartment, thereby for example preventing droplets from leaving the droplet inlet channel. As an illustrative example, the inlet member may include a hollow space at its lower end. Once inserted into a reservoir, the lower end of the inlet member may contact the base of the apparatus. The hollow space may then define the processing compartment. Thus, in some of these embodiments the inlet member also provides at least a part of the circumferential wall of the processing compartment and or the apparatus. In some of these embodiments the physical separation may allow for several processing compartments to be present within the same apparatus (cf. e.g. FIG. 1E).

The method of the invention furthermore includes providing a medium that is immiscible with the liquid droplet (supra). The method further includes disposing the medium into the processing compartment of the apparatus provided, such that the contraction included in the inlet member is immersed in the medium. As explained above, providing the apparatus includes in some embodiments providing an inlet member and disposing it into the reservoir of a suitable device. In one of these embodiments the medium is disposed into the processing compartment after the inlet member has been disposed therein. In another embodiment a device with a reservoir is provided first, thereafter the medium is disposed into the reservoir of the device, and subsequently the inlet member is disposed into the reservoir. The latter embodiment may for instance be chosen in order to avoid the formation of undesired air bubbles when providing the apparatus and filling liquid into the processing compartment thereof.

Where desired, a further medium may be added that is immiscible with the medium in the processing compartment, as long as it does not prevent or interfere with dispensing a desired liquid droplet therein. Another liquid of lower density may for example be added to the medium in the processing compartment, for instance to cover the surface of the medium in the processing compartment, e.g. in form of a layer. FIG. 12C depicts an illustrative embodiment, where a further medium is disposed onto the medium in the processing compartment, forming a layer on top thereof. In such embodiments the respective further liquid is typically selected to be immiscible with the medium in the processing compartment and maybe of lower density than the medium in the processing compartment. This may for instance be desired in order to prevent evaporation of the medium in the processing compartment. As an illustrative example, the medium in the processing compartment may be a hydroperfluoro carbon compound or a perfluorocarbon compound, and the liquid may be a layer of water. In such embodiments the method of the present invention thus includes providing a liquid which is immiscible with the medium (which may e.g. already be disposed in the processing compartment), and which is of lower density than that medium, and disposing the said liquid into the processing compartment of the apparatus.

In some embodiments the method of the invention further includes providing a surfactant and disposing the surfactant into the reservoir such that it is able to contact said medium and dissolve therein. Any surfactant may be used, typically the surfactant will be selected according to the medium in the processing compartment and the liquid of the droplet, since surfactants accumulate at surfaces. The surfactant may for instance be selected to lower the surface tension of the liquid of the droplet and/or where the medium is also a liquid, the surface tension of the respective liquid in the processing compartment. It may also be selected to lower or minimize interactions between the medium in the processing compartment and the inner walls thereof, such as the base or the circumferential wall(s). Typically the surfactant is an amphipathic organic compound, including an anionic, cationic, zwitterionic, or nonionic compound.

The surfactant may for instance be a hydrocarbon compound, a hydroperfluoro carbon compound or a perfluorocarbon compound (supra), which is substituted by a moiety selected from the group consisting of a sulfonic acid, a sulphonamide, a carboxylic acid, a carboxylic acid amide, a phosphate, or a hydroxyl group. Numerous perfluorocarbon-surfactants are for instance known in the art. Examples include, but are not limited to, pentadecafluorooctanoic acid, heptadecafluorononanoic acid, tridecafluoroheptanoic acid, undecafluorohexanoic acid, 1,1,1,2,4,4,5,5,6,6,7,7,8,8,9,9, 10,10,11,11,11-heneicosafluoro-3-oxo-2-undecanesulfonic acid, 1,1,2,2,3,3,4,4,5,5,6,6,6-tridecafluoro-1-hexanesulfonic acid, 2,2,3,3,4,4,5,5-octafluoro-5-[(tridecafluorohexyl)oxy]-pentanoic acid [Chemical Abstracts No 174767-00-1], 2,2,3,3-tetrafluoro-3-[(tri-decafluorohexyl)oxy]-propanoic acid] [CAS No 376-39-6], N,N'-[phosphinicobis (oxy-2,1-ethanediyl)]bis[1,1,2,2,3,3,4,4,5,5,6,6,7,7,8,8,8-heptadecafluoro-N-propyl-1-octanesulfonamide [the sodium salt has CAS No 82393-02-0], 1,1,2,2,3,3,4,4,5,5,6,6,7,7,8, 8,8-heptadecafluoro-1-octanesulfonic acid, 1,1,2,2,3,3,4,4,5, 5,6,6,7,7,8,8,8-heptadecafluoro-1-octanesulfonyl fluoride, [CAS No 190002-24-5], 2-[(β-D-galactopyranosyloxy)methyl]-2-[(1-oxo-2-propenyl)amino]-1,3-propanediyl carbamic acid (3,3,4,4,5,5,6,6,7,7,8,8,8-tridecafluorooctyl)-ester [CAS No 190002-24-5], 6-(3,3,4,4,5,5,6,6,7,7,8,8,8-tridecafluorooctyl hydrogen phosphate)-D-glucose, [the monosodium salt has CAS No 142740-63-4], 3-(3,3,4,4,5,5, 6,6,7,7,8,8,9,9,10,10,10-heptadecafluorodecyl hydrogen phosphate)-D-glucose [the monosodium salt has CAS No 142740-66-7], 2-(perfluorohexyl)ethyl isocyanate [CAS No 142010-49-9], 2,2,3,3,4,4,5,5,6,6,7,7,8,8,8-pentadecafluoro-N-phenyl-octanamide [CAS No 3316-17-4], 1,1,2,2,3, 3,4,4,5,5,6,6,7,7,8,8,9,9,10,10,11,11,12,12,12-pentacosafluoro-N-(2-hydroxyethyl)-N-propyl-1-dodecanesulfonamide [CAS No 84002-45-9], 2-methyl-, 2-[[(heptadecafluorooctyl)sulfonyl]methylamino]-2-propenoic acid ethyl ester [CAS No 14650-24-9], 3-(2,2,3,3,4,4,5, 5,6,6,7,7,8,8,8-pentadecafluoro-1-oxooctyl)-benzenesulfonic acid [the sodium salt has CAS No 131666-65-4], 3-(heptadecafluorooctyl)-benzenesulfonic acid [the sodium salt has CAS No 146444-79-3], 4-[(2,2,3,3,4,4,5,5,6,6,7,7,8, 8,8-pentadecafluoro-1-oxooctyl)amino]-benzenesulfonic acid [the monosodium salt has CAS No 176515-54-1], 3-[(o-perfluorooctanoyl)phenoxy]propanesulfonic acid [the sodium salt has CAS No 176515-56-3], N-ethyl-1,1,2,2,2-pentafluoro-N-(26-hydroxy-3,6,9,12,15,18,21,24-octaoxa-hexacos-1-yl)-ethanesulfonamide [CAS No 173219-11-9], 3-[ethyl[(heptadecafluorooctyl)sulfonyl]amino]-1-propanesulfonic acid [the sodium salt has CAS No 75032-81-4], 1,2,2,3,3,4,5,5,6,6-decafluoro-4-(pentafluoroethyl)-cyclohexanesulfonic acid [the sodium salt has CAS No 151017-94-6], 2-[1-[difluoro(pentafluoroethoxy)methyl]-1,2,2,2-tetrafluoroethoxy]-1,1,2,2-tetrafluoro-ethanesulfonic acid [the potassium salt has CAS No 70755-50-9], N-[3-(dimethyloxidoamino)propyl]-2,2,3,3,4,4-hexafluoro-4-(heptafluoropropoxy)-butanamide [CAS No 87112-48-9], N-ethyl-N—[(heptadecafluorooctyl)sulfonyl]-glycine [the potassium salt has CAS No 2991-51-7], or 2,3,3,3-tetrafluoro-2-[1,1,2,3,3, 3-hexafluoro-2-[(tridecafluorohexyl)oxy]propoxy]-1-propanol [CAS No 484001-47-0], to name a few.

Examples of perfluorocarbon-surfactants also include polymeric, compounds such as α-[2-[bis(heptafluoropropyl) amino]-2-fluoro-1-(trifluoromethyl)ethenyl]-ω-[[2-[bis (heptafluoropropyl)amino]-2-fluoro-1-(trifluoromethyl) ethenyl]oxy]-poly(oxy-1,2-ethanediyl) [CAS No 135089-94-0], α-[2-[[(nonacosafluorotetradecyl)sulfonyl] propylamino]ethyl]-ω-hydroxy-poly(oxy-1,2-ethanediyl) [CAS No 83995-63-5], polyethylene glycol diperfluorodecyl ether [CAS No 37382-58-4], α-[2-[ethyl[(heptadecafluorooctyl)sulfonyl]amino]ethyl]-ω-hydroxy-poly(oxy-1,2-ethanediyl) [CAS No 29117-08-6], α-[2-[ethyl[(pentacosafluorododecyl)sulfonyl]amino]ethyl]-ω-hydroxy-poly (oxy-1,2-ethanediyl) [CAS No 82397-47-5], α-[2-[[(heptadecafluorooctyl)sulfonyl]propylamino]ethyl]-ω-hydroxy-poly(oxy-1,2-ethanediyl) [CAS No 52550-45-5], N-(2,3-dihydroxypropyl)-2,2-difluoro-2-[1,1,2,2-tetrafluoro-2-[(tridecafluorohexyl)oxy]-ethoxy]-acetamide [CAS No 141483-28-5], α-(2-carboxyethyl)-ω-[[(tridecafluorohexyl)oxy]methoxy]-poly(oxy-1,2-ethanediyl) [the lithium salt has CAS No 496850-57-8], α-[2,3,3,3-tetrafluoro-2-[1,1,2,3,3,3-hexafluoro-2-(heptafluoropropoxy) propoxy]-1-oxopropyl]-ω-hydroxy-poly(oxy-1,2-ethanediyl) [CAS No 37541-12-1], and 2,3,3,3-tetrafluoro-2-(heptafluoropropoxy)-propionic acid polymer [CAS No 26099-32-1].

In one embodiment the surfactant has the structure $CF_3(CF_2)_m$—$(CH_2)_n$—$(OCH_2CH_2)_k$—OH, in which m is an integer from 3 to 100, n is an integer from 0 to 10, and k is an integer from 1 to 200. An illustrative example of a respective surfactant is α-(2,2,3,3,4,4,5,5,5-nonafluoropentyl)-ω-hydroxy-poly(oxy-1,2-ethanediyl) [CAS No 82397-48-6]. An illustrative example of a hydroperfluoro-surfactant is 1-deoxy-1-[(4,4,5,5,6,6,7,7,8,8,9,9,9-tridecafluoro-1-oxononyl)amino]-xylitol [CAS-No 487027-48-5].

The method further includes disposing the droplet into the droplet inlet channel of the inlet member. The disposed droplet is located below the contraction that is included in the droplet inlet channel. In some embodiments the contraction prevents the droplet from spontaneously passing through the droplet inlet channel. In this respect, it will be appreciated by those skilled in the art that the method of the present invention does not require relying on attractive forces between the apparatus of the invention and the liquid droplet. Such attractive forces that may assist or be relied on in the method of the invention include for example a surface with an affinity for a selected liquid droplet—such as for instance a non-polar base region or a non-polar inlet member used in combination with a non-polar liquid droplet, or, as a further example, capillary forces at a droplet inlet channel. Although an apparatus may be selected that allows for such attractive forces, alternative means may be used as explained above. As already explained, in some embodiments the contraction is for instance of smaller diameter than the diameter which the droplet has in the immiscible medium, which is filled into the processing compartment. In some embodiments an electric or an electromagnetic field may for instance be used, in particular where the liquid droplet has been charged (supra). Such an electric or electromagnetic field, including an alteration of properties such as the strength of the same, may also be used to further control the position of the liquid droplet. Particularly in embodiments where it is desired to alter the position of the liquid droplet—for instance where the liquid droplet is to be forced through the contraction of the droplet inlet channel—it may be desired to provide an apparatus that has surfaces with low or at least essentially no affinity to the liquid of the liquid droplet. Examples of a respective surface include, but are not limited to, the base region of the processing compartment and a surface of the inlet member. Selecting an apparatus with surfaces of such low affinity may avoid the action of undesired forces on the liquid droplet that may for instance interfere with altering the droplet's position.

Disposing the droplet into the droplet inlet channel may include disposing the droplet anywhere within or above the apparatus of the invention, including anywhere within or above the processing compartment. Disposing the droplet into the droplet inlet channel may include forming the droplet, typically by dispensing. As an example, the droplet may be dispensed above the contraction of the droplet inlet channel, such as for instance centrally or sideways above the inlet opening of the droplet inlet channel. In some embodiments of the method of the invention the droplet is dropped onto and/or directed into the immiscible medium that has been disposed in the processing compartment of the apparatus. In other embodiments the droplet is formed with the respective immiscible medium. In the course of all embodiments of the method of the invention the droplet is caused to be immersed in the immiscible medium. If the liquid of the droplet is of higher density than the immiscible medium, it thereafter sinks into the medium. Where it is of lower density, it floats on the surface of the medium or it ascends in the direction of the surface of the medium.

Where the droplet is dispensed, this may be carried out by any means. As an example, a dispenser may be provided. A dispenser may employ any suitable device or mechanism in order to provide and dispense a droplet of a desired size. Examples include, but are not limited to, piezoelectric pipettors, syringe pump-based pipettors, peristaltic pumps, touch-off dispensing, inkjet dispensing (including syringe-solenoid dispensing), and pin-transfer (cf. Rose, D, Drug Discovery Today (1999), 4, 411-419 for a review). By means of the dispenser the droplet may in one embodiment be disposed onto the surface of the immiscible medium without contacting the same, above an inlet opening of a droplet inlet channel of an inlet member. In another embodiment, for instance where the density of the droplet liquid is lower than the medium in the processing compartment, the droplet may be dispensed anywhere onto the surface of the immiscible medium (without contacting the same) and subsequently be positioned above an inlet opening of droplet inlet channel by means of a magnetic or an electric field (including an electrostatic field). In yet another embodiment the droplet may be dispensed directly onto the surface of a medium in a processing compartment by means of contact dispensing. Where desired, the dispensed quantities may be measured, e.g. by means of a camera as disclosed in US patent application 2003/0209560.

As indicated above, in some embodiments disposing the liquid droplet into the droplet inlet channel includes dispensing the liquid droplet into the processing compartment. The droplet may be dispensed from any location within the processing compartment, including the side walls or a device inserted into the processing compartment. It may be dispensed directly or indirectly into the droplet inlet channel, e.g. in a mechanical manner, below the contraction of the same. In some embodiments a nozzle of a dispenser may be inserted anywhere into the immiscible liquid in the processing compartment to dispense the droplet. Where the droplet is of lower density than the immiscible liquid, the nozzle may for instance be placed under a droplet inlet channel, so that the formed liquid droplet is driven upward under a contraction of a droplet inlet channel by buoyancy force. In some embodiments a dispensing tube, such as the nozzle of a dispenser, is directly inserted through the droplet inlet channel as depicted in FIG. 4F. As seen in FIG. 4F, the outlet of a respective dispensing tube may have a cross section that is smaller than the contraction. In such embodiments a droplet may be formed under the contraction with a droplet diameter that is larger than the maximally available diameter of the droplet inlet channel to pass, e.g. by means of buoyancy force. As two further illustrative examples for a dispensing tube, the droplet may be dispensed by means of a pipette tip or a capillary tube. The pipette tip or the capillary tube may be inserted into the droplet inlet channel, so that its opening reaches into the processing compartment. The respective dispenser may contain the liquid of the droplet and be designed or adapted to produce and break a drop at an outlet, such as the end of a tip, to form a droplet in a medium. To facilitate the breaking of a drop from the outlet of a dispenser, the surface of the dispenser can be coated with hydrophobic and/or oleophobic coating such as a perfluorocarbon film such as Teflon (cf. also above). In some embodiments, the dispenser of a liquid may be agitated briefly to break a drop from the end of the tip. Such methods of droplet release can be used individually or in combination.

In other embodiments a liquid can be dispensed indirectly into the droplet inlet channel. This can be achieved by exerting a mechanical force such as a positive pressure. As an illustrative example, a droplet of a liquid can be dispensed into the droplet inlet channel above the contraction thereof. Dispensing the droplet by means of pressure may apply a force on the liquid droplet that provides a velocity that is sufficient to allow the droplet to pass the contraction, thereby entering the processing compartment. In these embodiments, the kinetic energy of a respective droplet is higher than both the resistance of the medium and the deformation of the droplet at the contraction. Once the droplet has passed the contraction and enters the processing compartment, it is entrapped at the contraction and remains in the processing compartment.

Figure 3A:
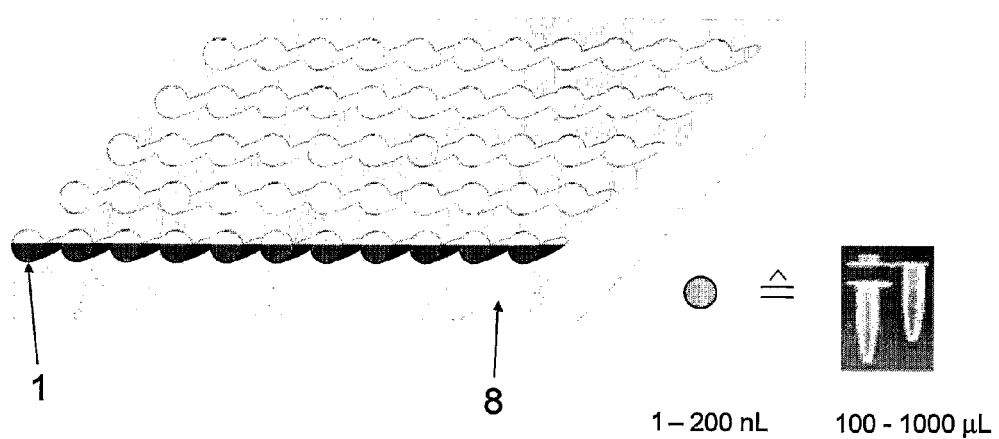
FIG. 3 shows schematically an array of samples in droplets when processed with an embodiment of the apparatus of the present invention (A), an example of dispensing an array of droplets (B), and an enlargement of a nozzle of two exemplary dispensers before or during dispensing a droplet (C, D).
Figure 3B:
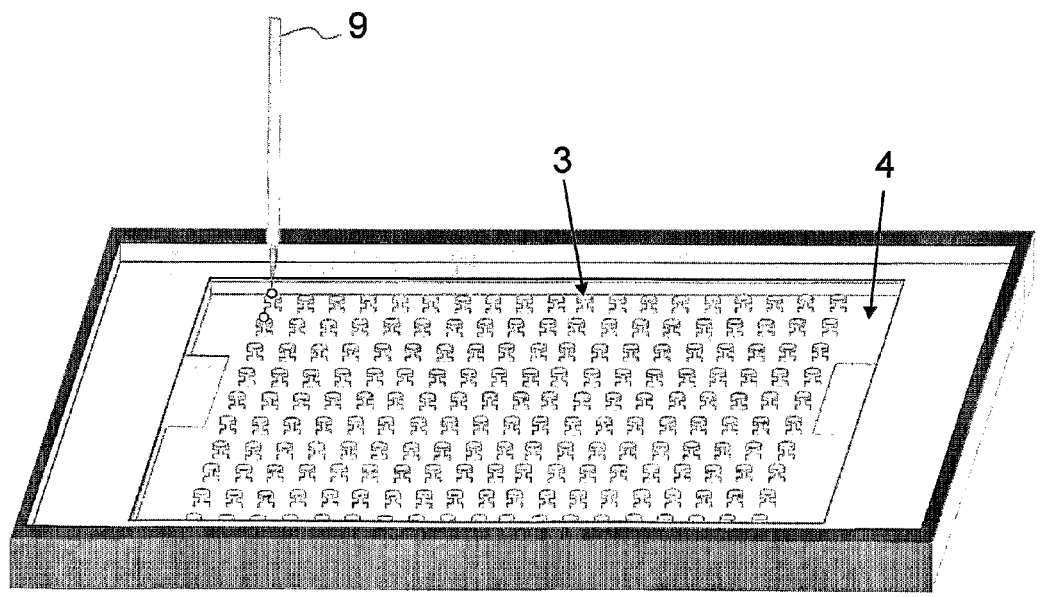
Figure 3C:
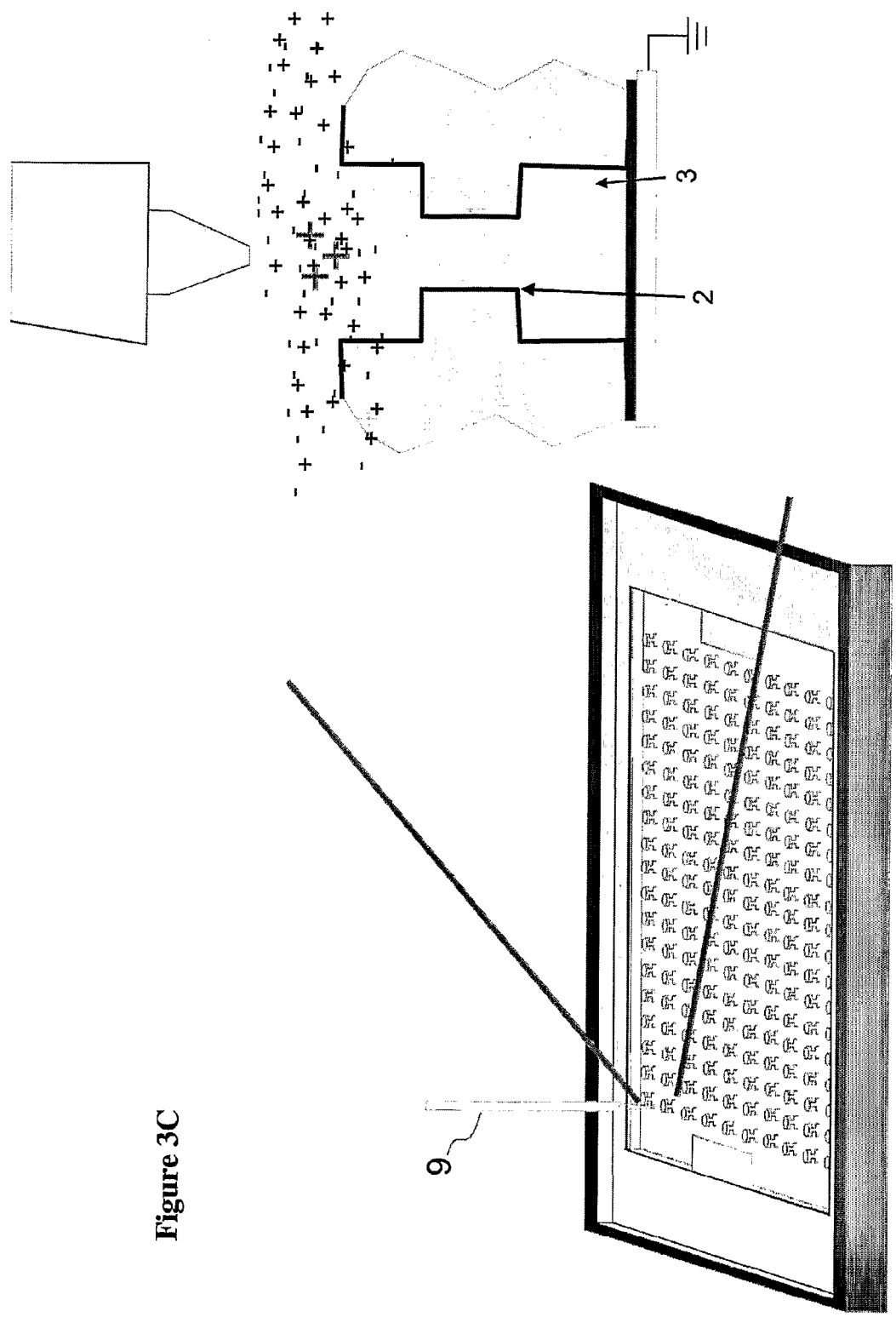

In some embodiments, the method also includes charging the liquid droplet (cf. FIG. 3C). In such embodiments the liquid droplet is typically charged before contacting the medium in the processing compartment, which is immiscible with the liquid droplet. In one of these embodiments, the liquid is being charged in a nozzle before being dispensed. In another embodiment the liquid droplet is dispensed first—for instance from a nozzle of a dispenser, whereafter the formed liquid droplet is being charged, for example by means of ionized air. Where desired, a certain liquid may be selectively charged, for example before being dispensed. A liquid may for instance be charged, whether before or after dispensing, by means of corona charging using a commercially available charger, such as Simco's V-Block electrostatic charger. It should be understood that, for charging, only charged ions from one electrode, either positive or negative, get released from a charger. Many charging devices are commercially available and where desired they can easily be adapted to provide a dispenser with a modification of interest.

In embodiments where the droplet is dispensed above the contraction of the droplet inlet channel, the method typically also includes allowing the liquid droplet to pass through the contraction into the droplet inlet channel, thereby transporting the droplet into the processing compartment. In one embodiment the method includes exposing the liquid droplet to an electric field, including an electrostatic field, such that the droplet is forced to pass through the contraction of the droplet inlet channel. Typically, in this embodiment the liquid droplet has been charged before (supra). In another embodiment the method includes exposing the droplet to a magnetic field such that the droplet is forced to pass through the contraction of the droplet inlet channel. In yet another embodiment the method includes exposing the droplet to both a magnetic and an electric field such that the droplet is forced to pass through the contraction of the droplet inlet channel. Where the contraction is of smaller diameter than the diameter which the droplet has in the immiscible medium, it is trapped under or above the contraction (supra). In another embodiment the droplet is allowed to pass through the contraction by means of gravity. Typically in this embodiment the droplet is heavier than the medium that is included in the processing compartment. In yet another embodiment allowing the liquid droplet to pass through the contraction includes exposing the droplet to any combination of an electric field, an electrostatic field, a magnetic field, and gravity. In some embodiments the process is only performed once the droplet has been allowed or forced to pass through the contraction and has entered the processing compartment. In some embodiments the droplet is allowed or forced to pass through the contraction and/or trapped by means of an electric/magnetic field. In some embodiments of the method, the electric/magnetic field is terminated, after the droplet is trapped above or below the contraction of the droplet inlet channel. Where desired, a liquid droplet may be neutralized after charging. This may for instance be desired to enhance the ability of controlling the position of the liquid droplet. Discharging can be performed by means of commercially available devices, such as Simco's V-Block electrostatic charger. For discharging, both positive and negative ion generators become active and generate ample charges of both signs for neutralization. It should be noted that for neutralization purposes, ample amounts of both positive and negative charges ought to be provided to a target object. Depending on the selected configuration of a charge generator and chip apparatus, neutralization can happen locally or throughout the entire chip apparatus.

In some embodiments of the method of the invention, exposing the droplet to an electric/magnetic field includes repelling the droplet. In some of these and in other embodiments exposing the droplet to an electric/magnetic field includes attracting the droplet. Attracting and/or repelling the droplet by means of an electric field may for instance be achieved by means of electrodes. In some embodiments a respective electrode is included in a device of the invention (supra), for example in form of an electro-chip (e.g. FIG. 4B). In some embodiments the droplet is charged before entering the immiscible liquid, for example by means of ionized air (cf. FIG. 3C). In some embodiments the droplet is charged before entering the immiscible medium.

In embodiments where a magnetic field is applied, the droplet may include magnetic particles. In such a case exposing the droplet to a magnetic field exerts a force on the magnetic particles, such that the droplet as a whole is forced to pass through the contraction of the droplet inlet channel. The droplet may be attracted or repelled by a magnetic field in a similar manner as a charged droplet in an electric field (including an electrostatic field). In some embodiments the magnetic field is applied before the droplet enters the immiscible medium. Where the droplet is larger than the available diameter of the contraction of a droplet inlet channel, the droplet is forced to pass the contraction by means of strong magnetic forces. Upon removal of the magnetic field, the droplet remains trapped above or below the contraction since the buoyancy force on the droplet is not strong enough to deform the droplet and move it through the contraction of droplet inlet channel. The magnetic particles used in such embodiments may provide a surface with an affinity for certain matter allowing for instance to absorb/adsorb proteins, peptides, nucleic acids and other compounds. Magnetic particles may contain ferromagnetic or supermagnetic material. Supermagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources such as Roche Applied Science, BIOCLON, BioSource International Inc. or Novagen Inc., to name a few. Magnetic nanoparticles based on supermagnetic Co and FeCo, as well as ferromagnetic Co nanocrystals have been described, for example by Hütten, A et al. (J. Biotech. (2004), 112, 47-63).

As described above, in some embodiments, the apparatus of the invention provides a plurality of inlet openings and/or contractions. In some of these embodiments the apparatus comprises a plurality of droplet inlet channels. Accordingly a respective apparatus may be used in the method of the present invention. Such embodiments of the method of the invention may include disposing a plurality of liquid droplets into the plurality of droplet inlet channels. A plurality of liquid droplet may for instance be dispensed below a plurality of droplet inlet channels, e.g. in a mechanical manner as described above. A single dispenser may for instance consecutively dispense liquid droplets at selected locations in a processing compartment, or a plurality of dispensers may be employed at a same time. As an illustrative example, one or more nozzles of one or more dispensers may be used to dispense a plurality of droplets into a plurality of droplet inlet channels, so that all, or a selected population of, the droplets are located below contractions of the plurality of droplet inlet channels. Where desired, disposing liquid droplets may be carried out in parallel. Each droplet of a respective plurality of liquid droplets may include a biological and/or chemical sample, for instance a sample from different origin. A process may be performed on any number of the samples in said plurality of liquid droplets. In some embodiments a different process is performed on different samples; in some embodiments the same process is performed on different samples. In one of these embodiments all samples are processed concurrently in parallel, so that a process, including a plurality of processes, is performed in the plurality of liquid droplets in parallel.

Any part of the method of the present invention may be performed in a manual or in an automated way, or in a combination thereof. Automated distribution of compounds, liquid and reagents, automated incubators and high-performance fluorescence readers, including plate readers, are already well established in the art. An example of the compatibility of the apparatus of the invention with standard laboratory equipment such as multi-well plates is illustrated in FIG. 2D. Typically, such equipment, e.g. multi-plate readers, -grippers, -fillers, -washers, or -stackers can directly be used with an apparatus of the present invention. As an illustrative example, any commercially available High-Throughput-Screening reagent dispensing robot may be employed to dispense liquid droplets into droplet inlet channels of the apparatus of the present invention. Where required, adaptations of either such equipment or of the apparatus of the invention to a particular application are easily performed by a person skilled in the art.

In order that the invention may be readily understood and put into practical effect, particular embodiments will now be described by way of the following exemplary embodiments and non-limiting examples.

EXEMPLARY EMBODIMENTS OF THE INVENTION

Exemplary embodiments of an apparatus and a method of the invention are shown in the appended figures.

Figure 1D:
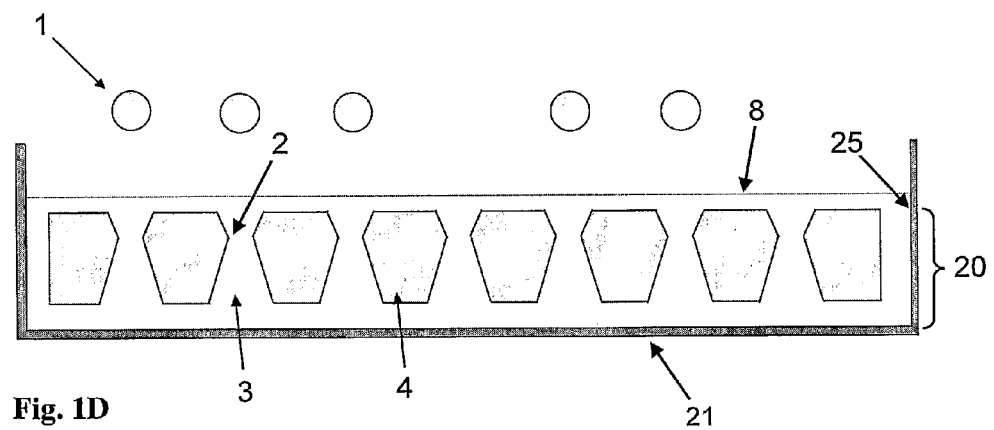
Figure 1E:
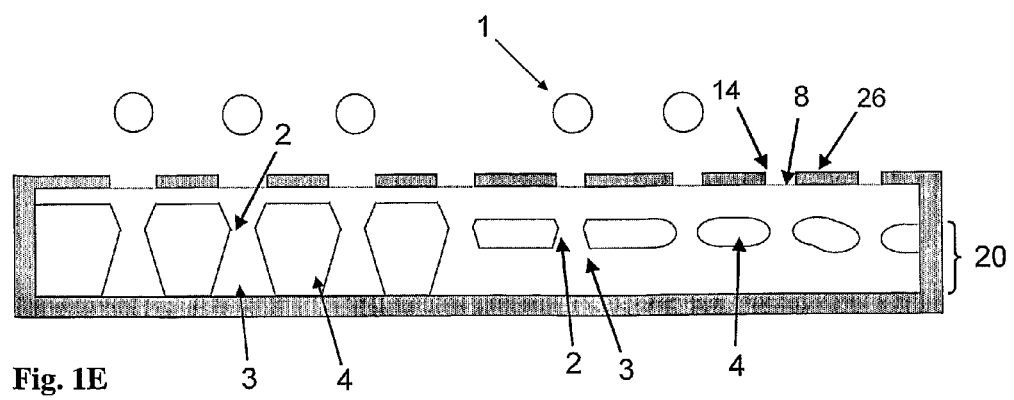

FIG. 1A depicts an embodiment of an apparatus according to the present invention for processing a sample in a droplet (1). The apparatus includes a processing compartment (20), which is defined by a base (21) and a lateral wall, which is a circumferential wall (25). An inlet member (4) is located on a top of the processing compartment (20). The inlet member (4) includes a droplet inlet channel (3). The droplet inlet channel possesses an inlet opening (28) and an outlet opening (27). In the droplet inlet channel (3) there is furthermore included a contraction (2). FIG. 1B depicts an apparatus, in which the inlet member (4), and thus also the droplet inlet channel (3), is of a height that is several-fold smaller than the diameter of the inlet channel (3), i.e. its dimension in the level parallel to the base. The apparatus is shown in a configuration accommodating a medium (8). The droplet inlet channel (3) is immersed in the medium (8). FIG. 1C depicts examples of profiles of the droplet inlet channel (3). The interior of the droplet inlet channel is depicted in grey. FIG. 1D shows an apparatus that includes a plurality of droplet inlet channels (3), each including a contraction (2). All droplet inlet channels (3) are identical and located in the same inlet member (4). The embodiment of the apparatus of the invention depicted in FIG. 1E also provides a plurality of droplet inlet channels (3) located in the same inlet member (4), each droplet inlet channel including a contraction (2). The droplet inlet channels (3) are of various profile. Furthermore the contractions (2) are located at different distances relative to the surface of medium (8). The apparatus also includes more than one processing compartment (cf. left side of the apparatus). The apparatus also includes a cover member (26), which provides a plurality of upper inlets (14) that provides fluid communication between the processing compartment and the environment of the apparatus, and into which droplets may be disposed.

Figure 2E:
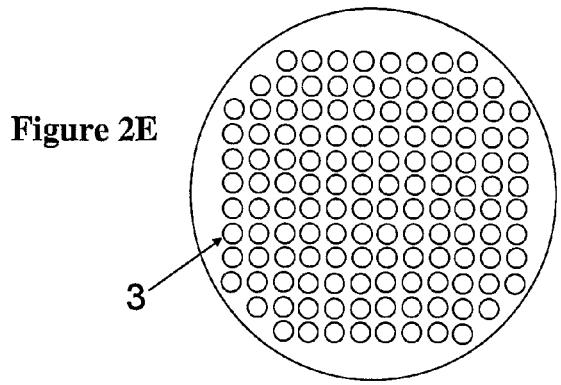
FIG. 2 depicts embodiments of an apparatus (A, B, C) of the invention where a chip is used (illustrated in D, E, F, G) to provide a plurality of contractions.
Figure 2F:
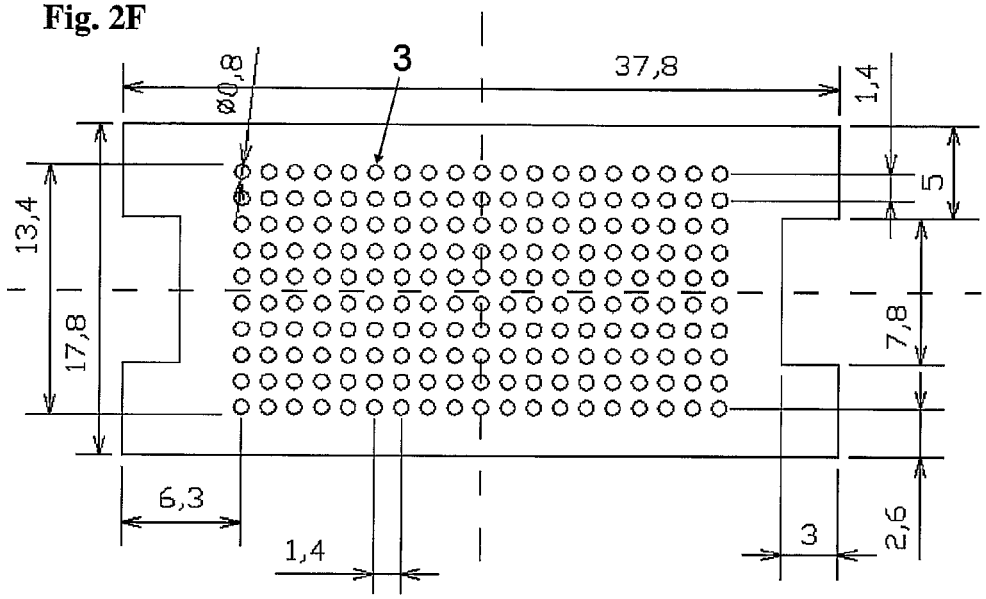
Figure 2G:
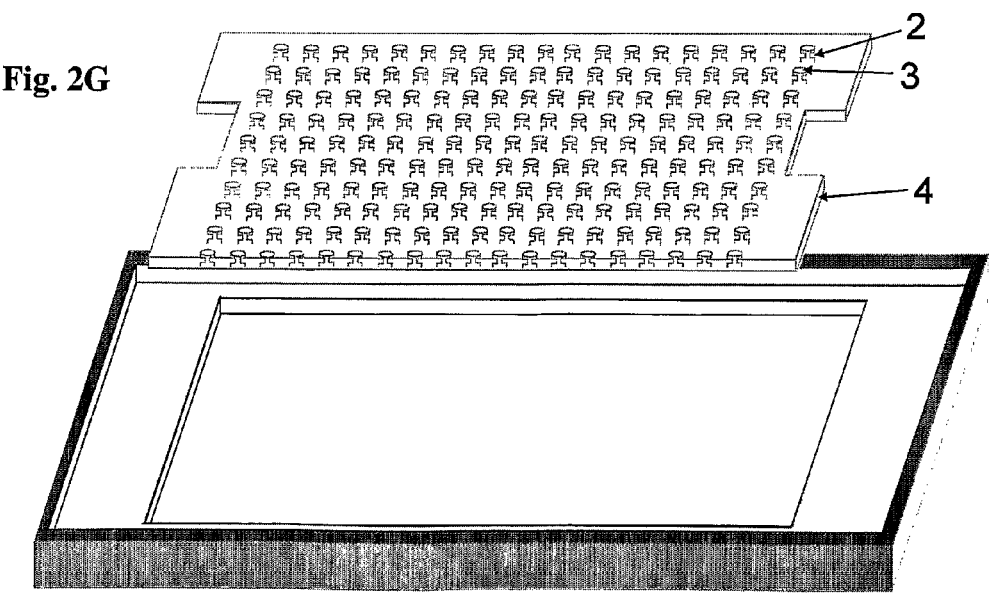

FIG. 2 depicts embodiments of an apparatus of the invention where a chip is used to provide a plurality of contractions. The apparatus includes a chip-holder, shown in cross-sectional view in FIG. 2A and in top view in FIG. 2B. The chip holder includes a reservoir (23) and a coverslip glass thin transparent plastic film (6) as a transparent base region. The circumferential wall (25) of the reservoir is adapted to support an inlet member in that it is extending into the interior of the reservoir, thereby forming a step by which an inlet member can be supported. FIG. 2C depicts the chip-holder with an inserted chip (4) and medium (8). FIG. 2D illustrates that a chip (4) may be chosen that matches the dimensions of a 96-well plate (5). It should however be noted that the dimensions of a contraction (2) of the apparatus of the invention are generally severalfold smaller than those of a well of a multi-well plate. It is understood that in other embodiments the contractions (2) are smaller than those depicted here. Nevertheless the inlet openings of the droplet inlet channels of a chip used in the apparatus of the invention may possess a diameter that resembles the diameter of a well of a 96-well plate. It should furthermore be noted that a chip as in some embodiments part of the apparatus of the invention does not possess wells with a bottom as a conventional multi-well plate (cf. e.g. FIG. 1D and FIG. 3A), but that it merely provides contractions of the apparatus. FIG. 2E and FIG. 2F show further embodiments of a respective chip that may be used to form the processing compartment of the apparatus of the invention. Only the droplet inlet channels (3) are represented by their inlet openings for better view. FIG. 2G illustrates how a chip (4) can be inserted into a chip-holder. The droplet inlet channels (3) of the chip (4) possess centrally located contractions (2), so that the droplet inlet channels (3) have the profile of an hourglass.

FIG. 3A illustrates schematically an array of samples when processed with an embodiment of the apparatus of the present invention. While in conventional devices such as multi-well-plates or reaction tubes the process volume is determined by the container used, in the apparatus of the present invention individual droplets (1) are exposed to a desired process. Accordingly, conventional devices are well suited for reaction volumes of about 10-about 1000 µl, but not for smaller volumes. In the apparatus and method of the present invention, droplets (1) immersed in a medium (8) may be of any volume. The process volume is thus for example determined by the dispenser used, as well as the properties of the liquid used and the medium in the processing compartment that is immiscible therewith. The method and apparatus are particularly well suited for volumes of about 10-500 nl.

FIG. 3B illustrates dispensing an array of samples, as shown in FIG. 3A, on top of droplet inlet channels (3) of a chip (4) in an apparatus of the invention. For this purpose a head of a dispenser (9) can be positioned above the respective droplet inlet channel (3).

FIG. 3C shows an enlargement of a nozzle of an exemplary dispenser (9), positioned above a droplet inlet channel (3) that includes a contraction (2). Ionized air (symbolized by charges "+" and "−") may be used to charge droplets, for example once they are disposed from the nozzle. A droplet is then charged before entering an inlet channel (3), including a contraction (2), of an apparatus of the invention. As a further example, a liquid in a nozzle may be charged before being released therefrom, e.g. through a nozzle. Upon dispensing, a droplet from a dispenser retains charges even after entering an inlet channel.

Figure 3D:
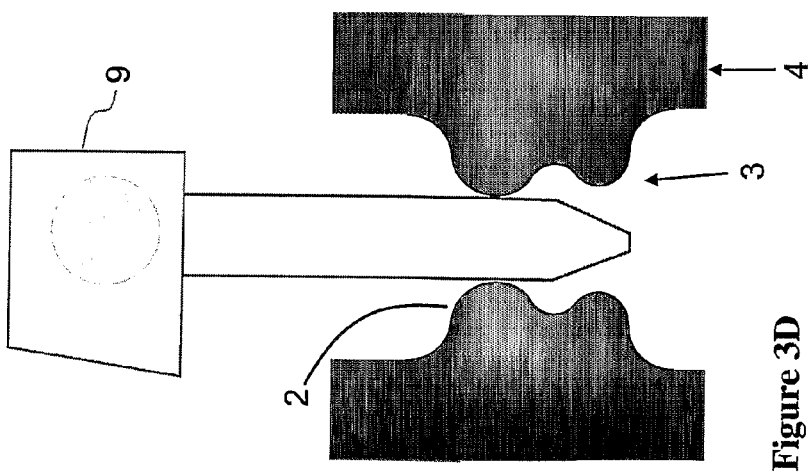

FIG. 3D shows an enlargement of a nozzle of a further embodiment of an exemplary dispenser (9). The dispenser is arranged in such a way that the nozzle is capable of reaching through the contraction (2) of the droplet inlet channel (3).

Figure 4A:
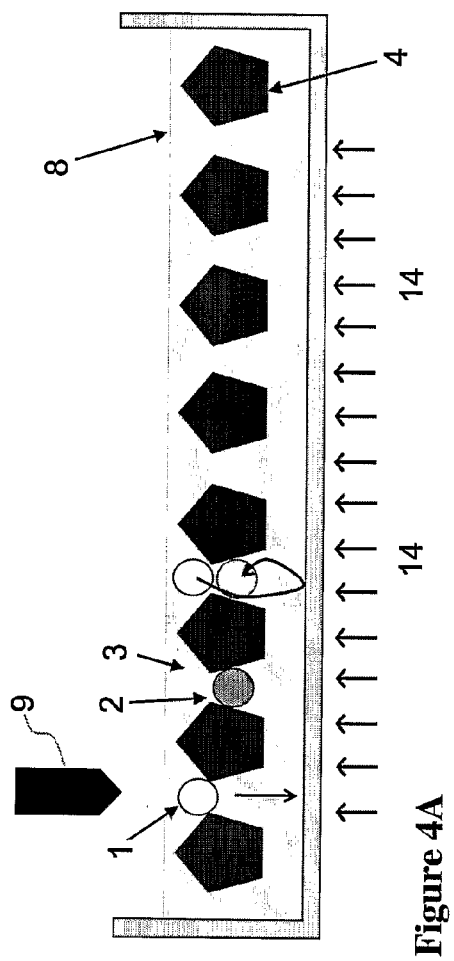
FIG. 4 schematically depicts how a droplet can be positioned and trapped by means of the method and apparatus of the present invention (A-F). It further illustrates the comparison of processes performed in a conventional tube ("bulk") and in a droplet in the apparatus of the present invention (G), as well as schematically a process that may be performed in the apparatus of the present invention (H).
FIG. 4G) and using the apparatus of the present invention (●), at enzyme concentrations of 0.1 ng/mL (A) and 1 ng/mL (B).

FIG. 4A depicts a scheme of dispensing a droplet (1) into an immiscible medium (8), forcing it through a contraction (2) in a droplet inlet channel (3) (cf. left hand side), and trapping the droplet under contraction (2). As can be seen, the contraction (2) is of a smaller diameter than the diameter which the droplet (1) has in the immiscible medium (8). The droplet inlet channel (3) is located in a chip (4). Optical detection (14) is performed to analyse a sample included in the droplet (1).

Figure 4B:
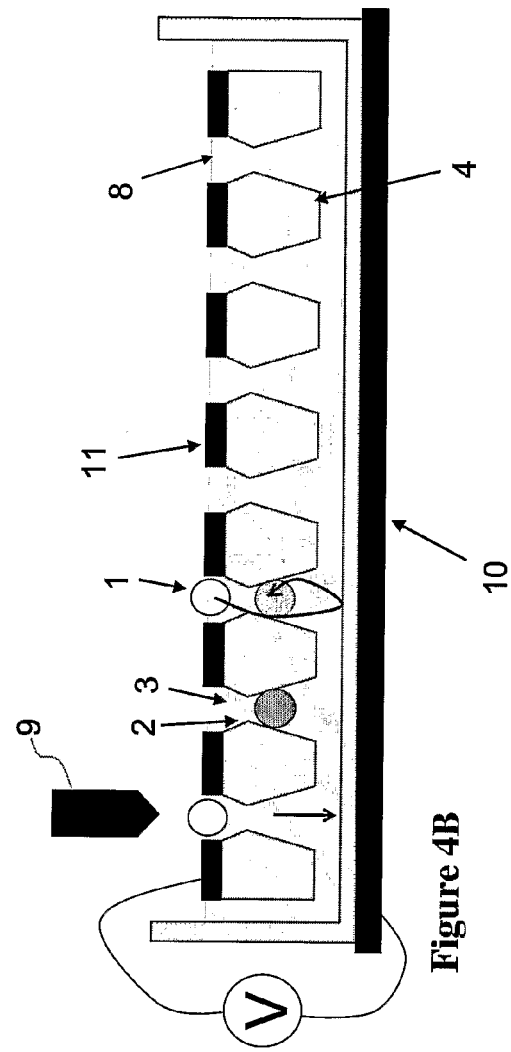

FIG. 4B depicts an exemplary scheme of forcing a droplet in an immiscible medium (8) through the contraction (2) in a droplet inlet channel (3) of a chip (4) by means of an electric field or a magnetic field (where the droplet includes magnetic material). The electric field is generated by means of an electrochip (11) and a planar electrode (10). Instead of the electrodes a magnet may be used, where it is desired to apply a magnetic field.

Figure 4C:
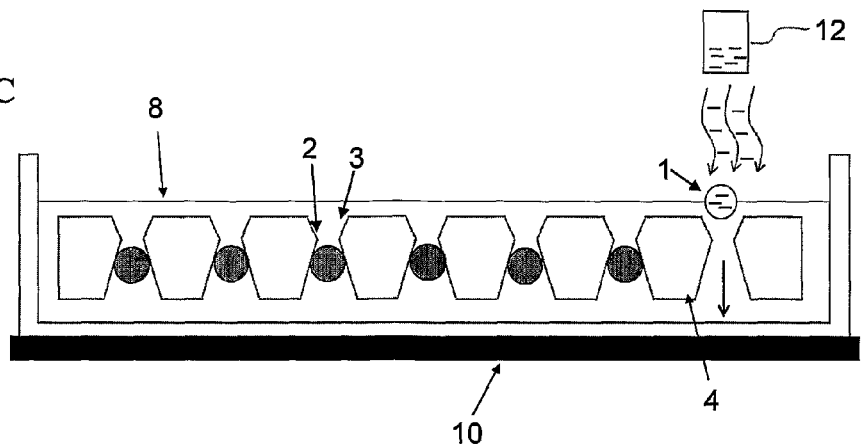

FIG. 4C depicts a further exemplary scheme of forcing a droplet in an immiscible medium (8) through a contraction (2) in a droplet inlet channel (3) of a chip (4) by means of an electric field. The electric field is generated by means of an external electrode (12) and a planar electrode (10).

Figure 4D:
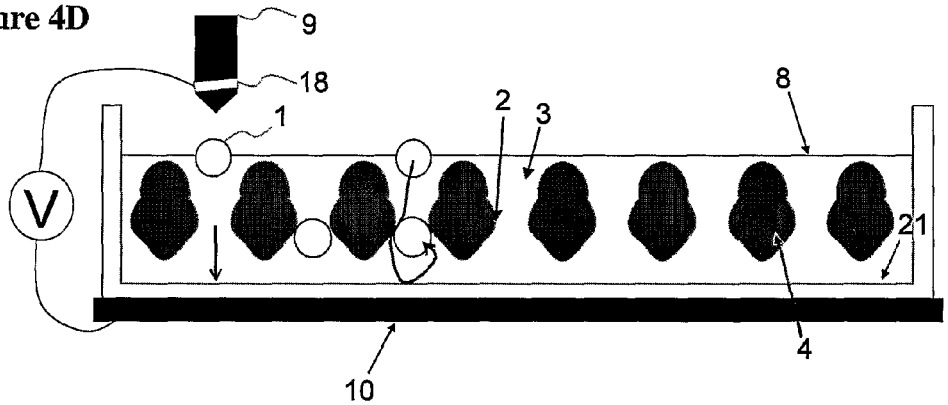

FIG. 4D depicts yet a further exemplary scheme of forcing a droplet (1) in an immiscible medium (8) through a contraction (2) in a droplet inlet channel (3) of a chip (4) by means of an electric field. The electric field is generated by means of wire wrapping (18) the tip of a dispenser and a planar electrode (10).

Figure 4E:
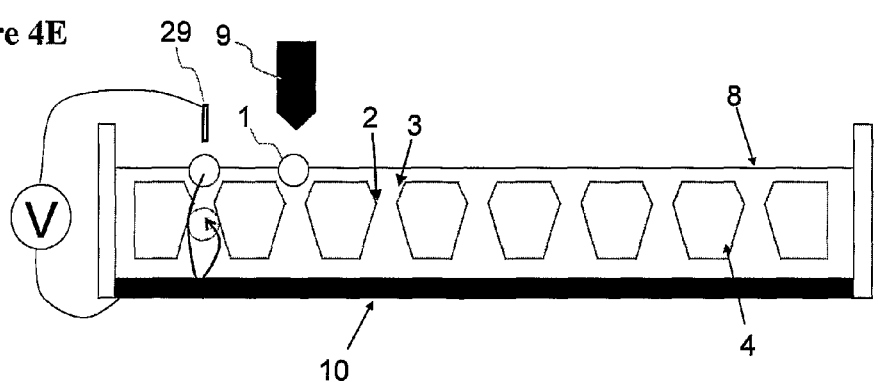
Figure 4F:
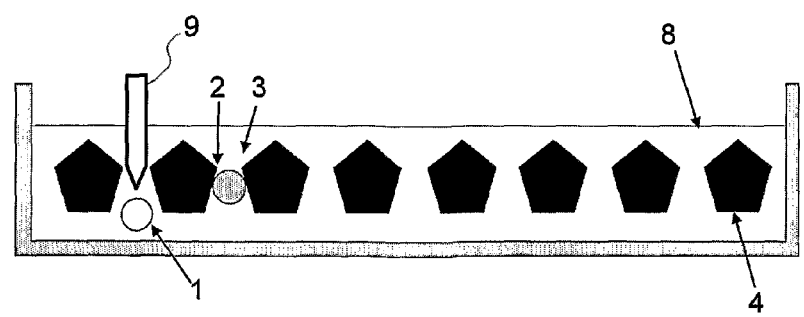

FIG. 4E depicts a further exemplary scheme of forcing a droplet (1) in an immiscible medium (8) through a contraction (2) in a droplet inlet channel (3) of a chip (4) by means of an electric field. The electric field is generated by means of a pointy electrode (29), which is adapted to be movable. Upon moving and positioning the pointy electrode (29) above a droplet floating above a droplet inlet channel, the electrode is activated so as to provide an electric field. This forces the droplet to enter the immiscible medium (8), to enter a droplet inlet channel (3) of the chip (4), and to pass the contraction of the droplet inlet channel (3).

FIG. 4F depicts schematically a further embodiment of entrapping a droplet (1) below a contraction (2) in a droplet inlet channel (3) of a chip (4). The nozzle of the dispenser (9) reaches through the contraction (2) of the droplet inlet channel (3) (cf. also FIG. 3D). Accordingly the droplet is dispensed into the immiscible medium (8) in the processing compartment below the contraction (2).

FIG. 4G illustrates the comparison performed in evaluating the method of the present invention. Processes were performed (cf. subsequent figures) in a conventional tube ("bulk") of a processing volume of about 40-100 μl and in a droplet (1) in the apparatus of the present invention. For processing in a conventional tube, premixing of the reaction mixture was performed in order to obtain a homogenous sample. The liquid in the droplets as well as the conventional tube was water, the medium immiscible with the liquid of the droplet was a liquid of a perfluoro carbon compound. The inlet member of the apparatus of the invention was a polytetrafluoroethylene (Teflon) plate (12).

FIG. 4H depicts schematically an exemplary process that may be performed in the apparatus of the present invention, a protease assay, such as a Caspase 3 fluorescence resonance energy transfer (FRET) assay. The vicinity of moiety "A" provides a quenching effect on the fluorescence signal of moiety "D", thus suppressing its dissemination. Upon cleavage of a peptide bond by a protease the quenching moiety "A" is released from moiety "D". As a consequence the fluorescence signal of moiety "D" can be detected.

FIG. 5 depicts the kinetic data of a β-Secretase assay in bulk condition (30 μL, □) in a conventional tube (cf. FIG. 4G) and miniaturized condition (60 nL, ●) at two different enzyme concentrations, in the absence of a surfactant. The enzyme concentration was 0.34 units/mL (FIG. 5 A) and 0.17 units/mL (FIG. 5 B). Reaction kinetics were similar for the method of the invention and the conventional bulk assay, regardless of the enzyme concentrations tested. This result illustrates the easy transferability of standard methods used in the art to miniaturized reaction volumes by the method and apparatus of the present invention, without the need of extended optimization experiments, as otherwise typically required in the art upon process down- or upscaling.

FIG. 6 depicts the inhibition assay of a Caspase assay performed in bulk condition (100 μL, ■) in a conventional tube (cf. FIG. 4G) and miniaturized condition (60 nL, ●) in the absence of a surfactant. The enzyme concentration was 0.1 ng/mL (FIG. 6 A) and 1 ng/mL (FIG. 6 B). Again data obtained by means of the apparatus and method of the present invention were comparable to those obtained using conventional laboratory equipment.

FIG. 7 depicts a photo of a 20 nl-droplet containing living cells, that may be used in a method and with an apparatus of the present invention. Labeling with a fluorescent viability stain may be used to show that the cells are alive and to verify that the apparatus is suitable for handling living cells. The cells are stained with Fluorescein-methylene-iminodiacetic acid (Calcein). This dye passes through the cell membrane of viable cells and thus proves the viability of the cultured cells.

FIG. 8 depicts a photo of a liquid droplet of cell culture media that includes adherent MC3T3 cells. The droplet further includes a 3-D matrix for the attachment of cells (BD Peptide-Hydrogel). The cells in the droplet are mixed with small air bubbles which were produced upon dispensing. A droplet as depicted can be disposed below a contraction in a droplet inlet channel of a chip.

Figure 9:
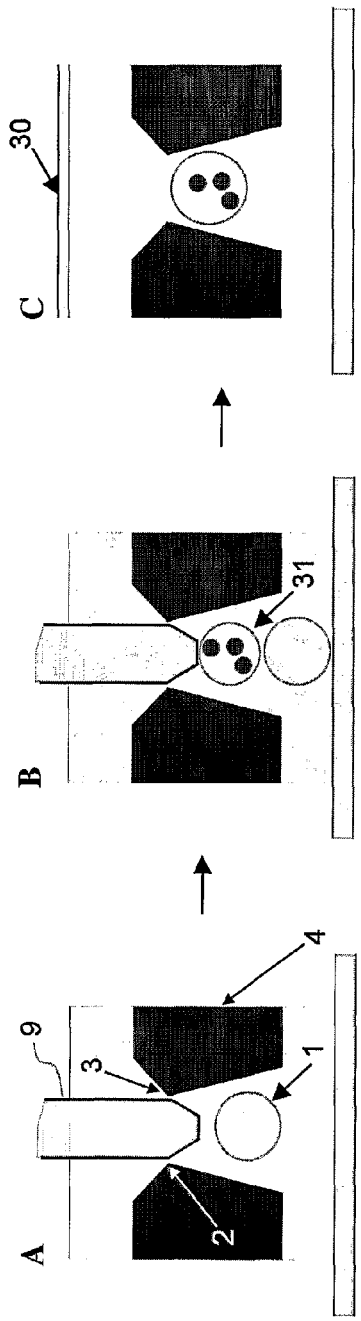
FIG. 9 schematically depicts how adherent cells can be cultivated using the method and the device of the invention (cf. also FIG. 4F). A droplet (1) with a 3-D matrix (A), and a droplet (31) of cells (B) are dispensed into a droplet inlet channel (3), where they merge.

FIG. 9 shows a scheme of an embodiment (cf. also FIG. 4F) of starting culturing cells using the method and the device of the invention. FIG. 9 A depicts entrapping a droplet (1), which includes a 3-D matrix for the attachment of cells (e.g. BD Peptide-Hydrogel), below a contraction (2) in a droplet inlet channel (3) of a chip (4). The droplet is dispensed directly into the processing compartment below the contraction (2). FIG. 9 B depicts entrapping a droplet (31), which includes cells, into the processing compartment below the contraction (2). FIG. 9 C depicts that the two drops merge due to the self-organizing nature of the droplet system, so that the cells get in contact with the 3-D matrix and can attach thereto. In the depicted embodiment a phase (30) of a liquid that is immiscible with the medium in the processing compartment, is furthermore disposed onto said medium.

Figure 10B:
FIG. 10A depicts non-adherent Thp-1 cells in a 9.5 nl droplet), in FIG. 10B enlarged for better view.
Figure 10A:

FIG. 10 shows non-adherent Thp-1 cells in a droplet that includes cell culture medium without an attachment matrix (as e.g. shown in FIG. 9A), that can be used in a method and with an apparatus of the present invention. FIG. 10A depicts a 9.5 nl droplet that includes non-adherent Thp-1 cells, which can be entrapped in the apparatus of the invention. The diameter indicated by a thin white bar was determined to be 289 μm. FIG. 10B depicts an amplified photo of cells within the droplet indicated by an arrow.

EXAMPLES

Example 1

Chip and Chip Holder of the Apparatus

The present example illustrates embodiments of a chip and a chip holder of a apparatus of the invention, in which a chip is positioned in a pocket of the holder and immersed in an immiscible medium. Depending of the liquid of the droplet and the immiscible medium used, the chip is made of an organic, inorganic or metallic substrate such as plastic, glass, silicon, or stainless steel, and has an array of droplet inlet channels of hour glass shape. The size of a model chip depicted in FIG. 2F is 37.8 mm×17.8 mm and has a 19×10 array of droplet inlet channels, which posses a maximum diameter of 800 μm and a contraction diameter of 300 μm. The profile of the droplet inlet channels corresponds to the first profile depicted on the upper left of FIG. 1C. A further chip has an array of droplet inlet channels of cylindrical shape, where the diameter of droplet inlet channel varies throughout the chip. The respective profile corresponds to the second from the left in the upper row of FIG. 1C. For example, the outer diameter of a droplet inlet channel can be 700-1200 μm and the neck diameter in the middle can be 300-600 μm. Most chips were made of polytetrafluoroethylene (Teflon), while other chips were made of plastic, such as polystyrene and coated with a perfluorocarbon silane film or perfluorocarbon film by plasma deposition. For the silane film, coating was performed by exposure to the heptadecafluoro-1,1,2,2-tetrahydrotrimethoxysilane vapour at 150° C. for 2 h after cleaning of the plate by sonication in basic detergent solution and thoroughly rinsing with deionised water. Alternatively, chips were dip-coated with a perfluorosilane and Teflon AF film. Alternatively, chips were coated with a perfluorocarbon or hydro-fluorocarbon film by plasma deposition. Chips made of polytetrafluoroethylene did not require a coating because the material itself provides a desirable hydrophobic and oleophobic surface.

The processing compartment is included in chip holders made of an organic, inorganic or metallic material such as plastic, glass, silicon, anodized aluminium or stainless steel. The processing compartment contains a pocket in the middle, which is capable of accommodating a chip. The base of the pocket includes a coverslip glass coated with a perfluorocarbon film or a comparable plastic plate coated with a hydro-fluorocarbon or perfluorocarbon film. The thin plates of some apparatuses are entirely coated with a perfluorocarbon film, while others are selectively coated in an exposed area. The treated coverslip glass is thin plates are glued to a chip holder frame. Around the edge of a pocket above a thin plate, there is a step of 0-500 μm thickness. This step functions as a spacer between a chip to be placed in the pocket and the thin plate. In some embodiments such a spacer is not required and a chip is directly placed on top of the bottom thin plate. A model chip holder depicted in FIGS. 2A and 2B has a size of 75 mm×25 mm and a height of 5 mm. In the middle, the holder has a pocket of 38 mm×18 mm capped with perfluorosilane-coated coverslip glass. At the bottom of the pocket, some chips posses a step of 0-300 μm thickness as a spacer between a chip and the coverslip glass.

Example 2

Liquid Handling

The immiscible medium may be a liquid, which is dispensed into the reservoir of a chip holder (cf. Example 1) so that it just fills half of the reservoir. Immiscible liquid can be mineral oil, silicone oil or perfluorocarbon liquid with or without appropriate hydrocarbon or perfluorocarbon surfactants. In most tests a perfluorocarbon liquid containing 0-10% perfluorocarbon-ethylene glycol surfactants was used. More specifically, perfluorocarbon liquid can be perfluorodecalin or Fluorinert™ available from 3M. The perfluorocarbon-ethylene glycol surfactant can be a compound with a structure of $CF_3(CF_2)_m-(CH_2)_n-(OCH_2CH_2)_k-OH$, in which m is an integer from 3 to 100, n is an integer from 0 to 10, and k is an integer from 1 to 200. In the compounds used typically m was an integer of 7-9, n an integer of 1-4 and k an integer of 1-200 (cf. Roach et al. supra, in particular the 'supporting information'). Upon addition of perfluorocarbon liquid, a chip is placed in a pocket slowly in order to prevent air bubbles in the chip, so that a reaction compartment is formed. The volume of perfluorocarbon liquid is just enough to cover the top surface of a chip. A reaction solution is dispensed into a droplet inlet channel covered with a thin layer of perfluorocarbon liquid by a non-contact dispenser. Since the densities of perfluorocarbon liquid and the aqueous solution are about 1.8-1.9 g/mL and ~1 g/mL, respectively, the dispensed solution floats on top of perfluorocarbon liquid in the form of a spherical droplet.

A dispensed droplet of a reaction solution can be moved to and retained in the lower part of the hour glass-shaped droplet inlet channel one-by-one or all together (FIG. 4A). A dispensed droplet is furthermore ionized by means of an ionizer, which generates a stream of either positive or negative ions and charges the droplet as well as nearby surroundings. Then, in the presence of an electric field present by the ionizer and/or electrochip located close to a chip the droplet (or a group of dispensed droplets) is moved downward into the processing compartment. The size of a dispensed droplet is bigger than the diameter of the contraction of the droplet inlet channel of the inlet member. The droplet deforms with the strong downward force, and passes through the contraction of the hour glass-shaped droplet inlet channel. Since buoyancy force is not strong enough for the droplet to pass the contraction of the droplet inlet channel, the droplet remains in the processing compartment, in the lower part of the droplet inlet channel, i.e. below the contraction, even in the absence of an electric field. Once the droplet is trapped, subsequent droplets can be added by dispensing regardless of their size. In a further embodiment, a droplet or a group of droplets can be ionized and repelled by the top electrode above to move to the lower part of a chip (FIG. 4B). Once a droplet moves to and remains in the lower part of a chip, the droplet is neutralized by the flow of either opposite charges or both negative and positive charges.

It is simple and straightforward to add and mix another reaction solution using the same approach. A solution to be added is dispensed into a droplet inlet channel and driven to the lower half of the droplet inlet channel. The new droplet easily merges with an existing droplet due to electrostatic attraction and physical similarity. Because the new droplet merges with an existing droplet bigger than the neck, the new droplet can be smaller than the neck. In hydrophobic and oleophobic perfluorocarbon liquid, aqueous droplets prefer to merge with each other instead of staying separate. Upon merging, mixing of solutions happens instantly due to the complex fluidics of liquid at the moment of merging and to the relatively small droplet sizes. Droplets immersed in perfluorocarbon liquid in a chip can be incubated for as long as needed because evaporation in the liquid is negligible during a typical incubation period.

Example 3

Electric Field for the Handling of Droplets

An electric field, including an electrostatic field, is a typical method for controlling a droplet in a perfluorocarbon liquid. Electrodes can be configured in many ways depending on the specific needs. In one configuration, an electro-chip with a footprint identical to an array of droplet inlet channels is placed on a sample chip and used as an electrode (FIG. 4C). The electro-chip can be made of a metal such as aluminium or stainless steel or a non-metal such as glass or silicon with metal coating. The other electrode of a flat slide is placed underneath a chip holder. The voltage applied to an electrode varies depending on the distance between the electrodes and the sizes of the droplet and droplet inlet channel. In general, a higher voltage is required as (a) the distance between electrodes increases, and as (b) the ratio of droplet size over neck diameter of a droplet inlet channel increases. For example, a voltage of 3 kV is required when two electrodes are 3 mm apart, the droplet size is 400 μm, and the diameter of the contraction of a droplet inlet channels is 300 μm.

In another configuration, a high-voltage ionizer is employed in order to charge a droplet on perfluorocarbon liquid. A droplet is moved down to the lower part of a chip by electrostatic repulsion. A chip holder is placed on a flat ground electrode and a high-voltage ionizer is positioned above the chip. A droplet is charged either by a positive or negative charge from the ionizer, and moves away from the ionizer by electrostatic repulsion. The presence of ground electrode below a chip holder can help such downward movement of the droplet. Once a droplet moves down, the whole system of chip and chip holder including dispensed droplets is neutralized by a flow of positive and negative charges (FIG. 4B).

In another configuration, one electrode (flat slide) is placed underneath a chip holder, and the other electrode (a thin circular wire) is placed around the tip of a dispensing nozzle (FIG. 4D). One electrode is positively or negatively charged, while the other electrode is grounded.

In a further configuration, one pointy electrode is placed right next to a dispensing nozzle, and the other electrode (flat slide) is placed underneath a chip holder (FIG. 4E). Upon dispensing a solution, the pointy electrode moves above a droplet inlet channel with a floating droplet and stays for less than 1 second to push the droplet to the other side of the droplet inlet channel. One electrode is positively or negatively charged, while the other electrode is grounded. The specific voltage applied can be optimized depending on the exact configuration.

In yet another configuration, one planar electrode is placed underneath a chip holder. The other electrode (a planar slide) big enough to cover the entire array area is brought close to an array of droplets from above after one series of dispensing is completed. One electrode is charged positively or negatively, while the other electrode is grounded. The voltage applied is optimized depending on the distance between electrodes, and the sizes of the droplets and droplet inlet channels.

Example 4

Optical Detection

For most biological applications, optical detection is used to analyze the process performed in the droplets. A chip holder is positioned in fluorescence microscope or Evotec Insight, an advanced confocal fluorescence microscope. Through a transparent coverslip slide at the bottom of a chip holder, the droplet held in each droplet inlet channel can be examined from below.

Example 5

Homogeneous Enzyme Assays

Two simple FRET-based protease assays (cf. the scheme of FIG. 4G), Caspase 3 and β-Secretase assays, have been selected as a model. The interface of perfluorocarbon liquid with and without perfluorocarbon surfactant was tested with these assays to examine the biocompatibility. Furthermore, logistics and functionality of the total system were evaluated while running the processes.

In an exemplary method with a model chip and chip holder, a solution of an enzyme, either Caspase 3 or β-Secretase, is dispensed onto perfluorocarbon liquid in a hole as a droplet of 40 nL. A 40-nL droplet has a diameter of 424 μm, which is slightly larger than the neck diameter of the droplet inlet channel (400 μm). Upon addition of a substrate solution of 40 nL, the droplet becomes 80 nL (535 μm in diameter). An inhibitor of different concentration can be added by programming a dispenser accordingly. In one example, an inhibitor of 10 different concentrations is added with the smallest dispensed drop size of 200 pL. Each inhibitor will be dispensed as a mixture with a buffer solution in the following combination by varying a number of dispensed droplets at a volume of 200 pL: Inhibitor+Buffer→10+0, 9+1, 8+2, 7+3, . . . , 1+9.

With ten 200-pL droplets in each concentration, the volume of each inhibitor solution becomes 2 nL. When an inhibitor is added to a droplet of an enzyme solution in a plate, a buffer solution is added first, followed by a corresponding amount of an inhibitor solution. This process is performed before the addition of substrate solution. After incubation, a stop solution is added if necessary, before examining each droplet by fluorescence microscopy.

Example 6

Non-Adherent Cell Assays

The human leukaemia cell line Thp-1 was used as a model for testing the logistics of the system, and the biocompatibility of the interface for cells.

Depending on the period of incubation, the non-adherent cell assay using the cell line Thp-1 requires a slightly modified work procedure, which can be easily optimized in a laboratory. For cell assays performed within a day, the assays can be performed in a similar manner as the enzyme assay described above. A cell solution is dispensed, followed by an inhibitor of different concentrations and a substrate, if necessary. For cultivation, the chip immersed in perfluorocarbon liquid is covered with a layer of aqueous solution such as DI water or PBS buffer. Due to the hydrophobic nature of the chip surface and presence of perfluorocarbon liquid, aqueous solution stays on the top of perfluorocarbon liquid in spite of density difference. The top aqueous layer helps to prevent evaporation of water from the droplets immersed in perfluorocarbon liquid during storage in an incubator. If the incubation takes less than a few hours, the aqueous layer on the top is unnecessary. At the end of the assay, each droplet is examined by optical detection. For cell assays incubated for more than a day, the chip needs additional perfluorocarbon liquid to immerse the chip completely, and a water layer on top of the perfluorocarbon liquid. The water layer on perfluorocarbon provides 100% relative humidity locally to prevent evaporation.

In other embodiments an oil such as silicone oil and mineral oil can be employed as an immiscible medium for cell-based assays. In one configuration, a medical-grade silicone oil is used as an immiscible liquid. Because the density of silicone oil (0.96 g/cm$^3$) is lower than that of water (1 g/cm$^3$), an aqueous solution droplet would sink down naturally and be positioned at the top of the coverslip glass of a chip holder.

Results and Discussion

In a droplet microarray system, aqueous droplets have direct contact only with the immiscible medium, not with the inner walls of the reaction compartment (formed by a chip holder) or the inlet member. All the surfaces of the inlet member, a chip, and the walls of the chip holder used that come into contact with an aqueous droplet, are coated with perfluorocarbon or a material of similar surface tension. An aqueous droplet appeared to prefer to be surrounded by perfluorocarbon liquid over the solid surface coated with perfluorocarbon, regardless of the presence of perfluorocarbon surfactants. Empirically, an aqueous droplet in the chip was never fixed to a certain position in a droplet inlet channel, confirming that a droplet does not adsorb onto a solid surface by direct contact.

The nature of a miniaturized assay in perfluorocarbon liquid has been investigated under simulated conditions and droplet microarray format. In simulated proof-of-concept studies, the performance of miniaturized assays in perfluorocarbon liquid was compared to that of bulk assays. An enzyme and substrate solutions of either Caspase 3 or β-Secretase assay was mixed in bulk, and part of the bulk solution was placed inside of a polytetrafluoroethylene (Teflon) tube immersed in perfluorocarbon liquid (FIGS. 5 and 6). In most tests, the volume of bulk solution placed in perfluorocarbon liquid was less than 100 nL. Upon completion of an assay, each assay solution in bulk and miniaturized condition was examined by confocal microscopy for the intensity of fluorescence signals. Both the kinetics and inhibition assays of the two model enzyme assays showed comparable performance for the assays in bulk and miniaturized conditions in the presence or absence of perfluorocarbon surfactants. FIG. 5 shows the kinetics of β-Secretase assay in bulk condition (30 μL) and miniaturized condition (<100 nL) at two different enzyme concentrations, in the absence of perfluorocarbon surfactants. The enzyme concentration was either 100% or 50% of that recommended by the supplier (Invitrogen). FIG. 5 illustrates that the kinetics of the bulk and miniaturized assays were similar, regardless of the enzyme concentrations tested. This result suggested no adverse effect associated with assay miniaturization.

FIG. 6 shows the inhibition assay of Caspase performed in bulk condition (100 μL) and miniaturized condition (<100 nL) in the absence of perfluorocarbon surfactants. The Caspase assay was performed in a similar manner to the β-Secretase kinetics assay. All the assay solutions were prepared in bulk, and part of the bulk solution was placed in a polytetrafluoroethylene tube immersed in perfluorocarbon liquid. The inhibition characteristics and $IC_{50}$ points were comparable for the bulk and miniaturized conditions at enzyme concentrations of 1 ng/mL and 0.1 ng/mL. This result suggested that miniaturization did not affect the performance of Caspase 3 assay.

Further studies were performed in order to investigate the impact of interface and electric field on enzyme assays. First, the effect of interface was examined by placing a droplet in direct contact with a solid surface of polytetrafluoroethylene (Teflon) or other material, while being immersed in perfluorocarbon liquid. The resulting assay showed that the enzymatic activity was reduced by 10-70% compared to that surrounded only by perfluorocarbon liquid. The poor performance of an assay in direct contact with a solid surface suggested that the interface has a major impact in miniaturization. In another set of experiments, assays run in miniaturized conditions were exposed to strong electric field and/or charging and discharging before incubation (cf. the scheme in FIG. 4F). These assays demonstrated similar performance as those run without electric field and/or charging and discharging. Overall, the results from this proof-of-concept study indicated that miniaturized enzyme assays in perfluorocarbon liquid performed as well as the bulk assays, regardless of the presence of perfluorocarbon surfactants and electric field.

The droplet microarray system was tested with an enzyme assay in order to confirm its compatibility with an assay. For example, a system of polytetrafluoroethylene (Teflon) chips was assembled in a chip holder to obtain an array of droplet inlet channels of 500 μm in width on the top, and 1000 μm in width at the bottom. A droplet was dispensed onto an inlet opening of a droplet inlet channel of 500 μm in width and forced to the lower part of a 1000 μm-wide droplet inlet channel. For β-Secretase assay, an enzyme solution of 60 nL was dispensed into a polytetrafluoroethylene chip, followed by 60 nL of substrate solution. After each dispensing, the array of droplets were exposed to positive charging to move the droplets down, to the lower part of a chip by electrostatic repulsion between the droplets and the charging electrode, and by electrostatic attraction between the droplets and the grounded electrode. When the droplets were retained in the lower part of the chip, they were then neutralized by a flow of positive and negative charges. After incubation of 2.5 hours, another 60 nL of stopping solution was added and mixed to stop the assay before examination under confocal fluorescence microscope. The fluorescence signals from the assays run at 30 μL and 120 nL were identical, suggesting that droplet miniaturization did not affect the performance of an assay at a scale of 120 nL. In addition, 3-dimensional scanning of droplet by confocal microscopy showed a perfect spherical droplet positioned in the center of the well. Thus, the droplet microarray platform offered an innovative tool in assay miniaturization, without compromising the data quality or the flexibility of liquid handling.

A droplet microarray for cell-based assays can be performed using a medical-grade silicone oil as the immiscible medium. In this configuration, droplets of 1-100 nL of Thp-1 cells can be dispensed into each droplet inlet channel of a polytetrafluoroethylene chip immersed in silicone oil. The cell viability may be confirmed using a dye, which provides green fluorescence for living cells (FIG. 7). The cell droplet arrays can also be applied towards drug testing by for instance dispensing genetically engineered cells with reporter genes and/or proteins.

What is claimed is:

1. An apparatus for processing a biological and/or chemical sample in a liquid droplet, the apparatus comprising a processing compartment, a base and at least one circumferential wall, wherein said processing compartment is defined by at least a part of said base, at least a part of said at least one circumferential wall, and an inlet member, wherein said inlet member is located on a top of the processing compartment, wherein said inlet member comprises at least one droplet inlet channel, said at least one droplet inlet channel extending through the inlet member and comprising a contraction between the inlet opening of the at least one droplet inlet channel to the environment and the outlet opening of the inlet channel to the processing compartment wherein the contraction is configured to be immersed in a medium that is immiscible with the liquid droplet.

2. The apparatus of claim 1, further comprising an upper inlet capable of providing a fluid communication between the processing compartment and the environment of the apparatus.

3. The apparatus of claim 1, wherein said contraction is adapted for preventing the droplet from spontaneously passing through the at least one droplet inlet channel.

4. The apparatus of claim 1, wherein said processing compartment is adapted to accommodate a medium.

5. The apparatus of claim 4, wherein said contraction is of smaller diameter than the diameter which said droplet has in said medium.

6. The apparatus of claim 1, wherein the profile of the at least one droplet inlet channel in the plane perpendicular to the base of the apparatus is of a shape selected from the group consisting of an hourglass, a concave semicircle, V-shape, a triangle, a rectangle, a square, any oligoedron and any combination thereof.

7. The apparatus of claim 1, wherein the at least one circumferential wall is a straight wall.

8. The apparatus of claim 7, wherein the straight wall is of a shape selected from the group consisting of cylindrical, horseshoe, and flat shape.

9. The apparatus of claim 1, wherein the at least one circumferential wall is adapted to support the inlet member.

10. The apparatus of claim 9, wherein the at least one circumferential wall is extending into the interior of the processing compartment, thereby forming a step by which the inlet member can be supported.

11. A method of processing a biological and/or chemical sample in a liquid droplet, comprising: providing an apparatus that comprises a processing compartment, a base and at least one circumferential wall, wherein said processing compartment is defined by at least a part of said base and at least a part of said at least one circumferential wall, and an inlet member, wherein said inlet member is located on a top of the processing compartment, wherein said inlet member comprises at least one droplet inlet channel, said at least one droplet inlet channel extending through the inlet member and comprising a contraction between the inlet opening of the inlet member to the environment, and the outlet opening of the inlet member to the processing compartment providing a medium that is immiscible with the liquid droplet, disposing said medium into the processing compartment of said apparatus such that said contraction is immersed in said medium; disposing said droplet into said at least one droplet inlet channel, such that it is located below said contraction comprised in said at least one droplet inlet channel; and performing a process on the biological and/or chemical sample in said droplet.

12. The method of claim 11, wherein said apparatus further comprises an upper inlet that provides a fluid communication between the processing compartment and the environment of the apparatus.

13. The method of claim 11, wherein said contraction of said apparatus prevents the droplet from spontaneously passing through the at least one droplet inlet channel.

14. The method of claim 13, wherein said contraction is of smaller diameter than the diameter which said droplet has in said medium.

15. The method of claim 11, wherein the profile of the at least one droplet inlet channel in the plane perpendicular to the base of the apparatus is of a shape selected from the group consisting of an hourglass, a concave semicircle, V-shape, a triangle, a rectangle, a square, any oligoedron and any combination thereof.

16. The method of claim 11, wherein the at least one circumferential wall is a straight wall.

17. The method of claim 16, wherein the straight wall is of a shape selected from the group consisting of cylindrical, horseshoe, and flat shape.

18. The method of claim 11, wherein disposing the droplet into said at least one droplet inlet channel comprises dispensing said droplet above the contraction of said at least one droplet inlet channel.

19. The method of claim 18, further comprising allowing the liquid droplet to pass through the contraction into said at least one droplet inlet channel, thereby transporting said droplet into the processing compartment.

20. The method of claim 19, wherein allowing the liquid droplet to pass through the contraction into said at least one droplet inlet channel comprises exposing the droplet to a force selected from the group consisting of an electric field, an electrostatic field a magnetic field, gravity and any combination thereof.

* * * * *